(12) United States Patent
Richey et al.

(10) Patent No.: US 11,167,256 B2
(45) Date of Patent: Nov. 9, 2021

(54) SYSTEM AND METHOD FOR MAKING MICROSPHERES AND EMULSIONS

(71) Applicant: OAKWOOD LABORATORIES, LLC, Oakwood Village, OH (US)

(72) Inventors: Tracy Richey, Kent, OH (US); Rachel Galaska, Chardon, OH (US); Samantha Cramer, Seven Hills, OH (US); Ford Minaghan, Coralville, IA (US); Cory Mahnen, Allentown, PA (US); Mark Smith, Venetia, PA (US); Fadee Mondalek, Clinton Twp, MI (US)

( * ) Notice: Subject to any disclaimer, the term of this patent is extended or adjusted under 35 U.S.C. 154(b) by 0 days.

(21) Appl. No.: 16/918,581

(22) Filed: Jul. 1, 2020

(65) Prior Publication Data

US 2021/0001290 A1    Jan. 7, 2021

Related U.S. Application Data

(60) Provisional application No. 62/869,220, filed on Jul. 1, 2019.

(51) Int. Cl.
| | | |
|---|---|---|
| *B01F 13/08* | (2006.01) | |
| *B01J 13/08* | (2006.01) | |
| *B01F 17/00* | (2006.01) | |
| *A61K 38/38* | (2006.01) | |
| *B01F 5/12* | (2006.01) | |

(Continued)

(52) U.S. Cl.
CPC ............ *B01F 13/08* (2013.01); *A61K 9/5089* (2013.01); *A61K 38/385* (2013.01); *B01F 3/0811* (2013.01); *B01F 5/12* (2013.01); *B01F 17/00* (2013.01); *B01J 13/08* (2013.01); *B01F 2003/0834* (2013.01)

(58) Field of Classification Search
None
See application file for complete search history.

(56) References Cited

U.S. PATENT DOCUMENTS

| | | |
|---|---|---|
| 4,459,245 A | 7/1984 | Ryon et al. |
| 4,536,092 A | 8/1985 | Abraham |

(Continued)

OTHER PUBLICATIONS

Tahnee J. Dening et al.; "Oral nanomedicine approaches for the treatment of psychiatric illnesses"; Journal of Controlled Release, vol. 223, 2016, pp. 137-156.

(Continued)

*Primary Examiner* — Jeffrey D Washville
(74) *Attorney, Agent, or Firm* — Benesch, Friedlander, Coplan & Aronoff LLP

(57) ABSTRACT

Various examples of systems and methods for making microspheres, microparticles, and emulsions are provided. In one example, a system and method for forming microspheres comprises: pumping a dispersed phase liquid and a continuous phase liquid into a levitating magnetic impeller pump to subject the dispersed phase liquid and continuous phase liquid to a high shear environment within the impeller pump's pump chamber. In another example, a system and method for forming an emulsion comprises: pumping a dispersed phase liquid and an inner aqueous phase liquid into a levitating magnetic impeller pump to subject the dispersed phase and the inner aqueous phase to a high shear environment within the impeller pump's pump chamber.

11 Claims, 34 Drawing Sheets

(51) Int. Cl.
   *B01F 3/08*   (2006.01)
   *A61K 9/50*   (2006.01)

(56) References Cited

U.S. PATENT DOCUMENTS

| | | |
|---|---|---|
| RE32,324 E | 1/1987 | Abraham |
| 5,705,196 A | 1/1998 | Galan Valdivia et al. |
| 5,945,126 A * | 8/1999 | Thanoo ............... A61K 9/1694 424/489 |
| 5,945,145 A | 8/1999 | Narsutis et al. |
| 6,054,145 A | 4/2000 | Vromans et al. |
| 6,224,794 B1 * | 5/2001 | Amsden .................... B01J 2/06 264/4.1 |
| 6,382,827 B1 | 5/2002 | Gebrian |
| 6,416,215 B1 | 7/2002 | Terentiev |
| 6,467,946 B1 | 10/2002 | Gebrian |
| 6,576,023 B2 | 6/2003 | Nakajima |
| 6,837,613 B2 | 1/2005 | Terentiev |
| 7,268,167 B2 | 9/2007 | Higuchi et al. |
| 7,479,859 B2 | 1/2009 | Gerber |
| 7,481,572 B2 | 1/2009 | Terentiev |
| 7,717,615 B2 | 5/2010 | Higuchi et al. |
| 8,104,951 B2 | 1/2012 | Aderhold et al. |
| 9,493,728 B2 | 11/2016 | Berrido et al. |
| 9,757,699 B2 | 9/2017 | Ahmed et al. |
| 9,863,423 B2 | 1/2018 | Bachellier |
| 10,005,677 B2 | 6/2018 | Lee et al. |
| 2005/0025630 A1 | 2/2005 | Ayre et al. |
| 2005/0161857 A1 | 7/2005 | Coombes et al. |
| 2007/0077155 A1 | 5/2007 | Shah et al. |
| 2013/0196375 A1 | 8/2013 | Strobbe |
| 2014/0066852 A1 | 3/2014 | Hassan et al. |
| 2014/0367003 A1 | 12/2014 | Williamson |
| 2016/0045502 A1 | 2/2016 | Brown |
| 2016/0250357 A1 | 9/2016 | Morales |

OTHER PUBLICATIONS

International Search Report and Written Opinion issued in PCT Application PCT/2020/040518, dated Sep. 21, 2020.

* cited by examiner

SYSTEM AND METHOD FOR MAKING MICROSPHERES AND EMULSIONS

CROSS-REFERENCE TO RELATED APPLICATIONS

This application claims priority to U.S. Provisional Patent Application No. 62/869,220, filed Jul. 1, 2019, which is incorporated by reference herein in its entirety.

BACKGROUND

Microparticles are small particles, with a size generally of about 1 to about 1000 micrometers (μm). Naturally occurring microparticles exist, such as pollen or dust. Microparticles can be made of numerous different materials depending on the application, including polymers, ceramics, and other materials.

Microspheres are generally spherical microparticles. In pharmaceutical applications, microspheres are often made out of natural, synthetic, or semi-synthetic polymers. Microspheres can be used in a multi-particulate drug delivery system to provide controlled or extended release drug delivery profiles. Such systems can be used in various oral dosage forms. Microspheres can also be used in injectable formulations. Microspheres as an extended release system can be useful for ease of patient use (i.e. fewer doses needed, making it easier for patient compliance), predictability of drug release, enhancing solubility of poorly soluble drugs, and may reduce gastrointestinal issues caused by some drugs if taken orally.

One way to form microspheres is to bring two streams (one aqueous stream and one organic stream) together in a high shear environment to create generally spherical polymeric microspheres. This high shear environment can be produced using a rotor/stator homogenizer, but such equipment in its many different possible configurations is inherently prone to the production of foreign particles due to the friction between the rotor, stator, bushing, and gaskets. The rotor speed and duration of the microsphere formation process affect the quantity of foreign particulate generation. Higher rotor speeds and longer durations tends to increase the quantity of foreign particulates in the final product, which is detrimental to product quality.

What is needed a system and method for producing microspheres that mitigates or eliminates the generation of foreign particulate matter.

SUMMARY

In one aspect, a system for forming microspheres is provided, the system comprising: a dispersed phase needle including: a dispersed phase input fitting at a first end, a needle tube at a second end, and a dispersed phase output fitting oriented between the dispersed phase input fitting and the needle tube, wherein the dispersed phase needle has a hollow bore; a tee or a wye including: a plurality of tubes, a tee input fitting or a wye input fitting, a continuous phase input fitting, and a continuous phase output fitting, wherein the tubes each include a hollow bore; and a pump chamber including: an input tube having an input fitting and a hollow bore, a housing, an output tube having an output fitting and a hollow bore, a hollow interior, and an impeller is oriented within the hollow interior, wherein the impeller includes a plurality of impeller blades and a base, wherein the base includes a magnet to magnetically engage a rotating magnetic field outside of the pump chamber, and wherein the impeller rotates and creates a direction of natural flow of a fluid through the pump chamber in a direction from the output tube toward the input tube.

In another aspect, a system for forming microspheres is provided, the system comprising: a tee or a wye including: a plurality of tubes, a tee input fitting or a wye input fitting, a continuous phase input fitting, and a continuous phase output fitting, wherein the tubes each include a hollow bore; and a pump chamber including: an input tube having an input fitting and a hollow bore, a housing, an output tube having an output fitting and a hollow bore, a hollow interior, and an impeller oriented within the hollow interior, wherein the impeller includes a plurality of impeller blades and a base, wherein the base includes a magnet to magnetically engage a rotating magnetic field outside of the pump chamber, and wherein the impeller rotates and creates a direction of natural flow of a fluid through the pump chamber in a direction from the output tube toward the input tube; and wherein a dispersed phase liquid is pumped through at least one of the plurality of tubes of the tee or the wye and into the hollow interior of the pump chamber in a direction opposite the direction of natural flow, wherein a continuous phase liquid is pumped through the tee or the wye and into the hollow interior of the pump chamber in a direction opposite the direction of natural flow, and wherein the dispersed phase liquid and the continuous phase liquid are homogenized in a high shear environment created by rotation of the impeller within the hollow interior of the pump chamber.

In another aspect, a method for making microspheres is provided, the method comprising: providing a dispersed phase source; providing a continuous phase source; providing a levitating magnetic impeller pump including: a pump chamber having a hollow interior, an impeller including a plurality of impeller blades, and wherein the impeller is oriented within the hollow interior and wherein the rotation of the impeller creates a direction of natural flow of a fluid; pumping the dispersed phase under positive pressure into the pump chamber of the levitating magnetic impeller pump via the pump's intended output in a direction opposite the direction of natural flow; pumping the continuous phase under positive pressure through a tee or a wye and into the pump chamber via the pump's intended output in a direction opposite the direction of natural flow; and homogenizing the dispersed phase and the continuous phase within the pump chamber.

In another aspect, a method for making an emulsion is provided, the method comprising: providing a dispersed phase source; providing an inner aqueous phase source; wherein the ratio of the inner aqueous phase to the dispersed phase is between 1:1 and 1:80; combining the dispersed phase and the inner aqueous phase in an emulsion vessel to form a mixture; providing a pump; providing a levitating magnetic impeller pump including: a pump chamber having a hollow interior, an impeller including a plurality of impeller blades, and wherein the impeller is oriented within the hollow interior and wherein the rotation of the impeller creates a direction of natural flow of a fluid; pumping the mixture under a positive pressure into the pump chamber of the levitating magnetic impeller pump via the pump's intended output in a direction opposite the direction of natural flow; removing the mixture from the pump's intended input and returning the mixture to the emulsion vessel.

In another aspect, a method for producing microspheres or microparticles using a levitating magnetic impeller pump is provided, the method comprising: wherein the levitating magnetic impeller pump includes a pump chamber having a hollow interior, and a rotating impeller contained within the hollow interior of the pump chamber; wherein a dispersed phase liquid or dispersed phase suspension is pumped into the hollow interior of the levitating magnetic impeller pump's pump chamber; wherein a continuous phase liquid is pumped into the hollow interior of the levitating magnetic impeller pump's pump chamber; and wherein the dispersed phase liquid and the continuous phase liquid are homogenized in a shear environment created by rotation of the impeller within the hollow interior of the pump chamber.

BRIEF DESCRIPTION OF THE DRAWINGS

The accompanying figures, which are incorporated in and constitute a part of the specification, illustrate various example systems, apparatuses, and methods, and are used merely to illustrate various example aspects. In the figures, like elements bear like reference numerals.

DETAILED DESCRIPTION

Described herein is a novel method to create microspheres within the housing of a levitating magnetic impeller pump. In one aspect, an organic stream is pumped into the chamber in the opposite direction intended by the pump manufacturer. That is, what is intended by the impeller pump manufacturer as an input is used in the method described herein as an output; what is intended by the impeller pump manufacturer as an output is used in the method described herein as an input. However, while the input and output are used opposite how the manufacturer intended, the pump impeller is operated in the direction intended by the manufacturer. In this manner, the impeller pump may be used as a homogenizer. Surprisingly, a levitating magnetic impeller pump that is designed to create a low shear environment within its pumping chamber may be made to act as a homogenizer producing a high shear environment within its chamber by operating the pump in a manner that is opposite its natural direction of flow. This opposite operation may be achieved by pumping a CP and DP through the levitating magnetic impeller pump in the opposite direction as intended by the manufacturer.

Alternatively, an organic stream is pumped into the chamber in the same direction intended by the pump manufacturer and microspheres are created.

Figure 1:
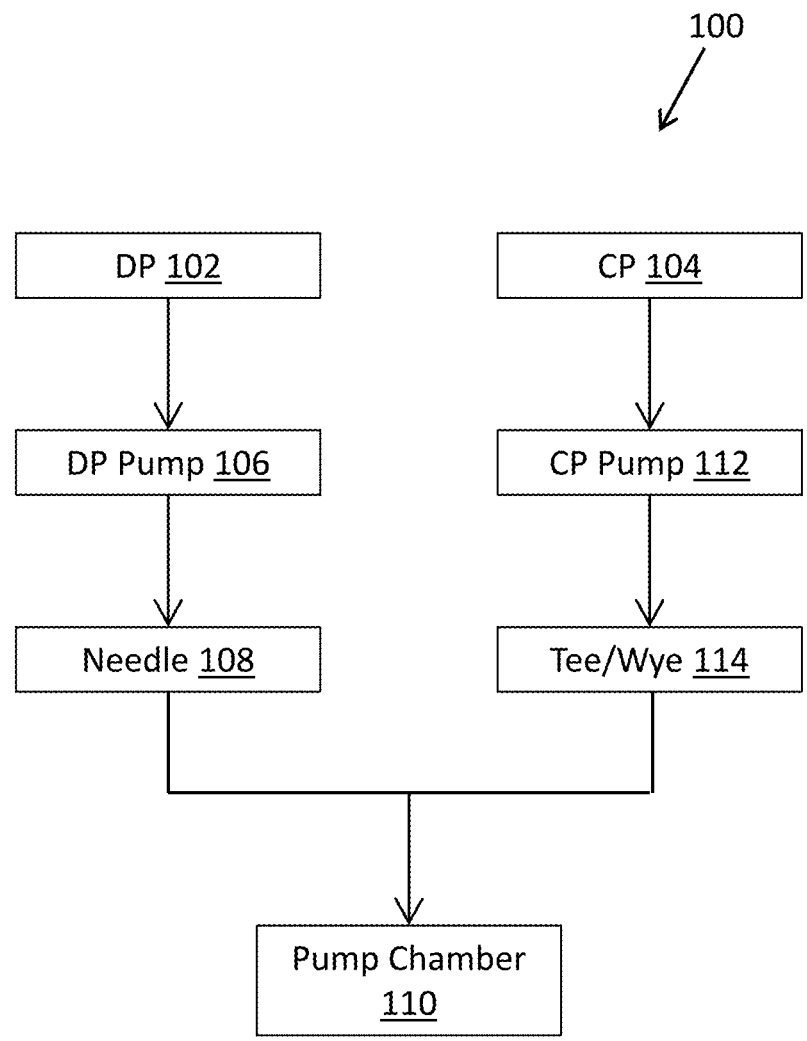
FIG. 1 is a schematic illustrating a system 100 for producing microspheres.
Figure 2:
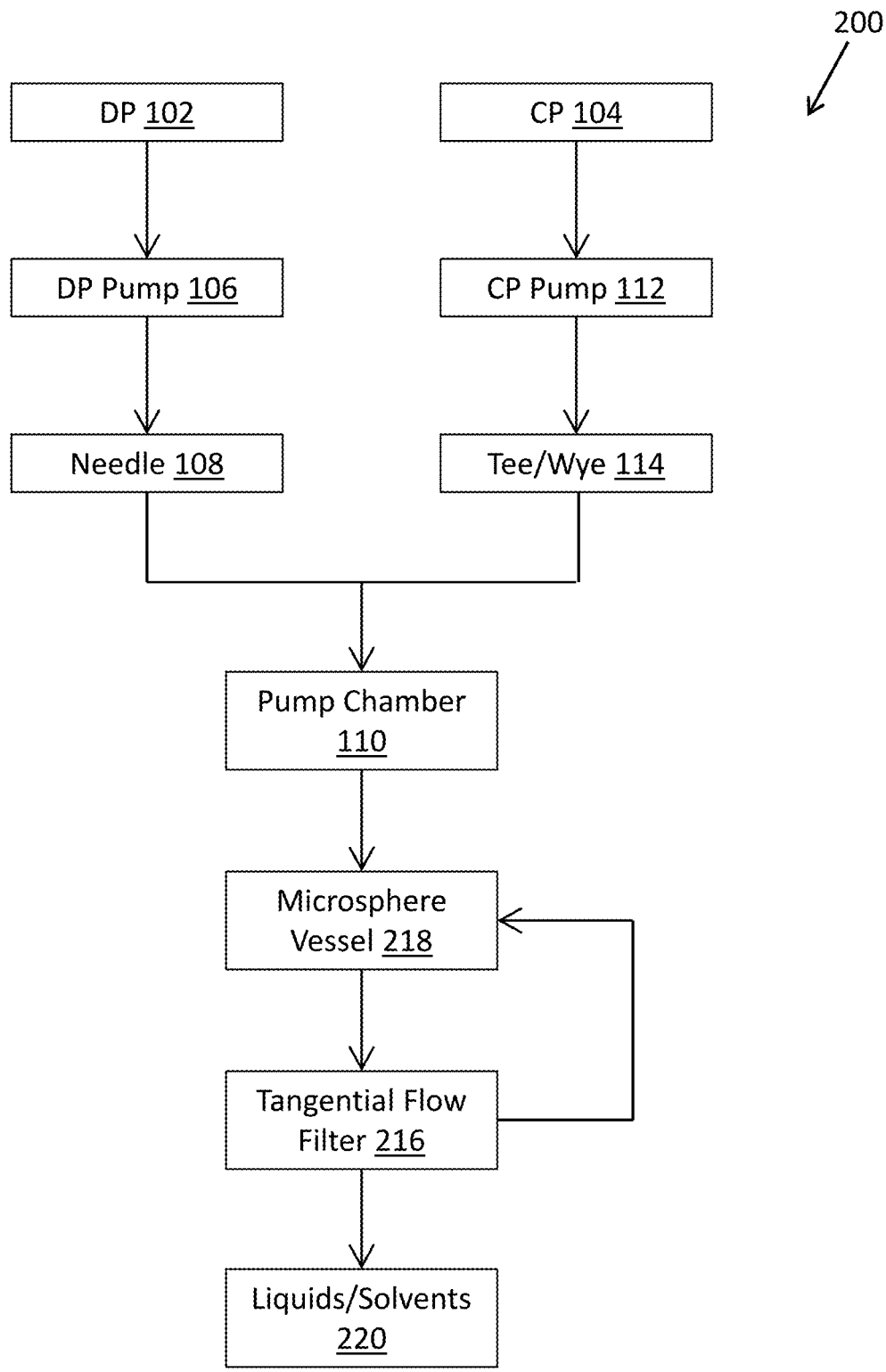
FIG. 2 is a schematic illustrating a system 200 for producing microspheres.

The formation of microspheres occurs inside the pump chamber (used as a mixing chamber in the method described herein), which contains a rotating levitating impeller that is not in contact with any other surface. To clarify, the levitating magnetic pump's pump chamber is used in the methods herein as a mixing chamber, including where the pump is operated in a direction in the reverse of its natural flow (the pump impeller is operating in its intended direction, but the fluids pumped through the pump flow in a direction opposite the pump's natural flow). A rotating magnetic field is created outside the sealed pump chamber and is directed to the inside of the pump chamber, causing levitation and rotation of the impeller. The use of magnetic forces enables the formation of microspheres in the sealed pump chamber that is free of contacting parts present in rotor stator homogenizers, because no such rotors or other such parts are present in the chamber, but rather only the levitating impeller driven by the magnetic forces is contained within the chamber. As such, the microspheres are formed while foreign particulate matter is eliminated, or at least greatly reduced as compared to manufacturing of microspheres with a rotor stator homogenizer.

As described above, a levitating magnetic impeller pump may be used as a homogenizer to form microspheres. A levitating magnetic impeller pump is a pump that contains a levitating impeller within the chamber of the pump that is not in contact with any surface. Rather, the levitating impeller is rotated using magnetism. More specifically, a rotating magnetic field is created outside of the sealed chamber and is directed to the inside of the chamber, causing levitation and rotation of the impeller. Examples of such levitating magnetic impeller pumps include the Levitronix® models BPS i100, BPS 600, BPS 2000, PuraLev-100SU, PuraLev-600SU, and PuraLev-2000SU. In normal operation (when used as a pump, as intended by the manufacturer), a levitating magnetic pump may create a low-shear environment within the pump chamber. However, when used in the method described herein, wherein the intended output of the pump is used instead as an input, and wherein the intended input of the pump is used instead as an output, a high-shear environment is created within the chamber, which is thereby used as a mixing chamber.

Throughout the application, the concept of pushing a solution through a levitating magnetic pump "in reverse of its intended operation," "backward," "opposite its intended operation," and the like is frequently referenced. The levitating magnetic pump may be engineered to, in its intended/normal operation, create a low shear environment within the pump chamber, where a fluid such as a liquid is drawn into the pump chamber (i.e., via a negative pressure generated by a rotating impeller at the input) via the pump's intended input, and pushed out of the pump chamber (i.e., via a positive pressure generated by a rotating impeller at the output) via the pump's intended output. This direction of flow/pumping is the natural, designed direction of flow of the levitating magnetic pump when used as intended. When used "in reverse," "backward," "opposite," etc., the levitating magnetic pump still operates in its standard direction (i.e., the rotating impeller continues to rotate in the direction intended by the manufacturer), but a liquid (such as a solution) is forced into the pump's intended output at a pressure greater than the positive pressure generated by the rotating impeller at the output. In this manner, the fluid overcomes the levitating's magnetic pump's pumping ability, and the manufacturer's intended output becomes an input, while the manufacturer's intended input becomes an output. The fluid forced into the pump's intended output is pressurized to a positive pressure that is greater than that which the levitating magnetic pump generates, and the fluid may be pressurized by any of a variety of mechanisms, including for example a separate and independent pump.

The materials used for the impeller and the housing of the pump chamber are, in one aspect, preferably biocompatible (i.e. compliant with FDA and USP-VI, ABSE/TSE free and animal free) resins. In such an arrangement, it can be ensured that no such non-biocompatible material is introduced to the microsphere product.

When using the levitating magnetic impeller pump to form microspheres, the microspheres may be formed by bringing together two streams (one aqueous stream and one organic stream) in the high-shear environment within the pump chamber to create spherical polymeric microspheres. As described above, the two streams are pumped through the pump chamber in a direction opposite that intended by the pump manufacturer in its instructions, but the levitating magnetic impeller is operated in its intended direction. The organic stream may also be known as the "dispersed phase" or "DP" and the aqueous stream may also be known as the "continuous phase" or "CP."

The DP may comprise a variety of solutions comprised of polymers, active pharmaceutical ingredients, and organic solvents. Exemplary polymeric compounds that may be used include poly(lactic-co-glycolic acid) (PLGA), PLGA-PEG (PLGA and polyethylene glycol co-polymer), PEG (polyethylene glycol), cellulosic polymers, polycaprolactone, polyglycolide, polylactic acid (PLA), poly-3-hydroxybutyrate, polyhydroxyalkanoates, polyesteramide (PEA), polyanhydrides, polyacetals, poly(ortho esters), polyphosphoesters, polyureas, and polycarbonates. Examples of organic solvents may include methylene chloride, (also known as dichloromethane or DCM), ethyl acetate, acetic acid, acetone, acetonitrile, acetyl acetone, acrolein, acrylonitrile, allyl alcohol, 1,3-butanediol, 1,4-butanediol, 1-butanol, 2-butanol, tert-butanol, 2-butoxyethanol, n-butyl amine, butyl dioxitol acetate, butyraldehyde, butyric acid, 2-chloroethanol, diacetone alcohol, diacetyl, diethylamine, diethylene glycol diethyl ether, diethylene glycol dimethyl ether, diethylene glycol monobutyl ether, diethylene glycol monobutyl ether acetate, diethylene glycol monoethyl ether, diethylene glycol monoethyl ether acetate, diethylene glycol monomethyl ether, N,N-diethylnicotinamide, dimethyl sulfoxide, N,N-dimethylacetamide, N,N-dimethylformamide, 1,4-dioxane, 2-ethoxyethanol, 2-ethoxyethyl acetate, ethyl acetate, ethyl formate, ethylene glycol methyl ether acetate, formic acid, furfural, glycofurol, hexylene glycol, isobutanol, isopropyl alcohol, 2,6-lutidine, methyl acetate, methyl ethyl ketone, methyl isopropyl ketone, methyl propionate, N-methylpyrrolidone, morpholine, tert-pentanol, 2-picoline, 3-picoline, 4-picoline, piperidine, 1-propanol, propionaldehyde, propylene oxide, pyridine, pyrimidine, pyrrolidine, tetrahydrofuran, tetramethylurea, triacetin, triethylene glycol, and trimethyl phosphate, and combinations thereof. These lists of polymers and solvents are not intended to be exhaustive, and any polymer and solvent that could be used for making microspheres by the prior high shear mixer methods may be usable in the present inventive methods.

The CP may comprise at least water. Optionally, a surfactant may be included. Examples of such optional surfactants may include polyvinyl alcohol (PVA), polyvinylpyrrolidone (PVP), calcium stearate (CSt), and methyl cellulose.

FIG. 1 is a schematic illustrating a system 100 for producing microspheres. System 100 may include a DP source 102 (e.g., a reservoir) operatively connected to a DP pump 106 configured to positively pressurize DP to force DP through a DP needle 108 and into the pump chamber 110 of a levitating magnetic impeller pump. System 100 may include a CP source (e.g., a reservoir) operatively connected to a CP pump 112 configured to positively pressurize CP to force CP through a tee/wye 114 and into pump chamber 110.

FIG. 2 is a schematic illustrating a system 200 for producing microspheres. System 200 is the same as system 100, except for the addition of a directing the suspension created in pump chamber 110 to a microsphere vessel 218. The suspension in microsphere vessel 218 may be directed to a tangential flow filter 216. Tangential flow filter 216 may separate the microspheres and the liquids/solvents from the solution, directing the microspheres to microsphere vessel 218, and directing the liquids/solvents to a liquids/solvents container 220. The solution may be circulated from vessel 218, to tangential flow filter 216, and back to vessel 218 one time, or multiple times, as may be necessary to remove the liquids/solvents to container 220. Tangential flow filter 216 may include any of a variety of filters, including for example a hollow fiber filter. Alternatively, any method of dewatering the solution created in pump chamber 110 is contemplated, and such methods are not limited to the use of a tangential flow filter, hollow fiber filter, or the like.

Figure 3:
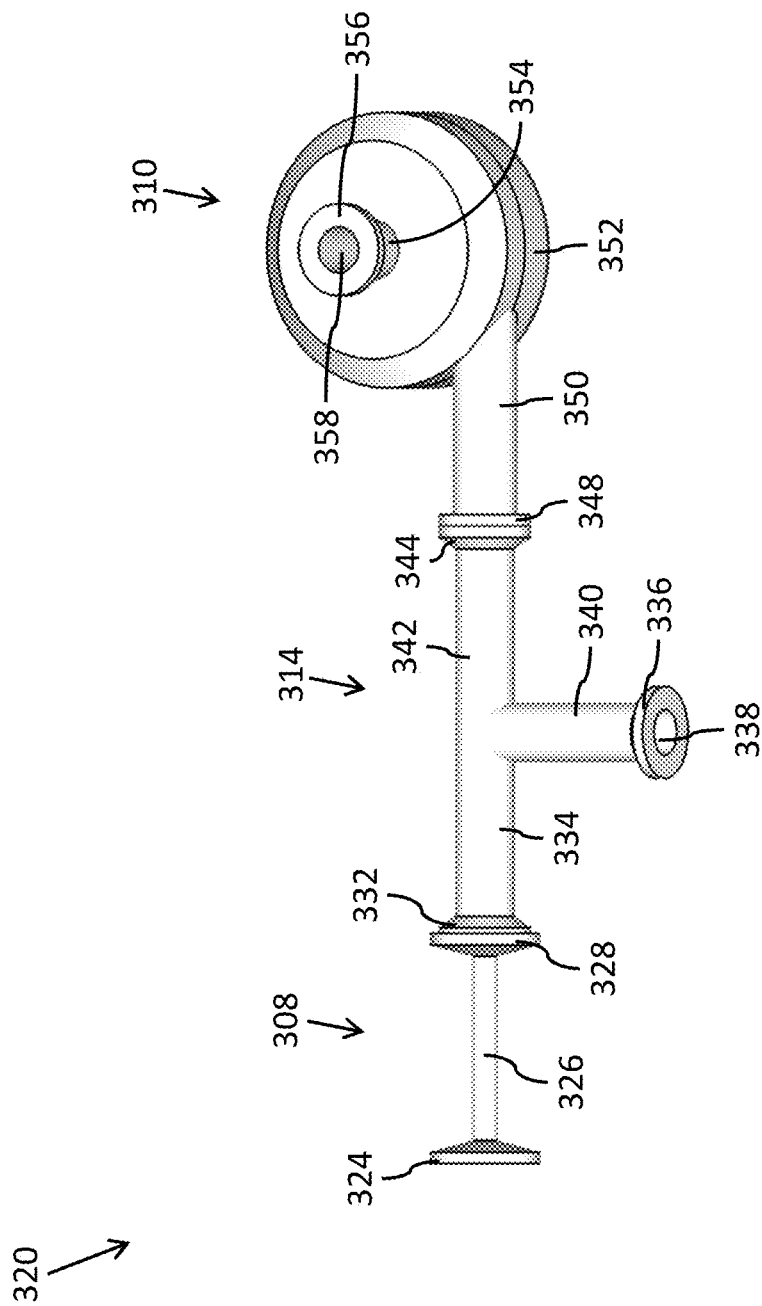
FIG. 3 is a perspective view of a microsphere formation system 320.

FIG. 3 is a microsphere formation system 320. System 320 may include a DP needle 308, a tee 314, and a pump chamber 310.

DP needle 308 may be formed of any of a variety of materials, including for example a metal (e.g., stainless steel) or a polymer.

DP needle 308 may include a DP input fitting 324 at a first end, and a needle tube (illustrated as 460 in FIGS. 4A-4C) at a second end. Input fitting 324 may engage a corresponding fitting or other connector from a supply line or DP pump to create a seal preventing a liquid, fluid, or air from escaping from the engagement of input fitting 324 with the corresponding fitting or other connector. Fitting 324 may be connected to a tubular member 326, which in turn may be connected to a DP output fitting 328. Output fitting 328 may engage a tee input fitting 332 or other fitting on tee 314 to create a seal preventing a liquid, fluid, or air from escaping from the engagement of output fitting 328 and the corresponding input fitting 332. A bore (462 in FIG. 4C) or perforation extends through input fitting 324, tubular member 326, output fitting 328, and the needle tube (460 in FIGS. 4A-4C). Bore 462 thus permits the passage of a liquid or other fluid through the entirety of DP needle 308 from input fitting 324 at a first end and out the end of needle tube 460 at a second end.

Tee 314 may be formed of any of a variety of materials, including for example a metal (e.g., stainless steel) or a polymer.

Tee 314 may include a generally T-shaped member formed from three tubes (first tube 334, second tube 340, and third tube 342). First tube 334 and third tube 342 may be coaxial in arrangement. First tube 334 and third tube 342 may actually be different ends of the same tube, and second tube 340 may simply butt into the combined first and third tube. Tee input fitting 332 may be connected to a first end of first tube 334. A CP input fitting 336 may be connected to a first end of second tube 340. A CP output fitting 344 may be connected to a first end of third tube 342. First tube 334, second tube 340, and third tube 342 may be connected to one another at their second ends, or alternatively, where first tube 334 and third tube 342 are actually different ends of the same tube, the combined first/third tube is connected to second tube 340 at the second end of second tube 340, at a location somewhere along the length of the combined first/third tube. Each of the tubes may include a hollow bore, and each of the hollow bores may be in fluid communication with one another. Second tube 340 includes a hollow bore 338. First tube 334 and third tube 342, being coaxial, may share a bore (illustrated as 564 in FIGS. 5A and 5B).

CP input fitting 336 may engage a corresponding fitting or other connector from a supply line or CP pump to create a seal preventing a liquid, fluid, or air from escaping from the engagement of CP input fitting 336 with the corresponding fitting or other connector. In practice, CP is positively pressurized by a CP pump, causing CP to flow into tee 314 at input fitting 336, through bore 338, through bore 564, and flow out of tee 314 at CP output fitting 344. CP cannot flow out of tee 314 at tee input fitting 332 due to the seal created between tee input fitting 332 and DP output fitting 328.

CP output fitting 344 may engage pump chamber 310's input fitting 348. Input fitting 348 may be what is intended as an output by the pump manufacturer. The engagement between CP output fitting 344 and input fitting 348 may create a seal preventing a liquid, fluid, or air from escaping from the engagement of CP output fitting 344 and input fitting 348.

Pump chamber 310 may be formed of any of a variety of materials, including for example a polymer or a metal (e.g., stainless steel).

Pump chamber 310 may include an input tube 350 connected to and extending between input fitting 348 and a housing 352. Pump chamber 310 may include an output tube 354, connected to housing 352 and an output fitting 356. Input tube 350 includes a hollow bore (illustrated as 666 in FIGS. 6B and 6C). Output tube 354 includes a hollow bore 358. As discussed further below, pump chamber 310 is a sealed unit with a hollow interior within which an impeller rotates, creating a high-shear environment. Output fitting 356 may engage a corresponding fitting or other connector on a supply line, filter, or vessel to create a seal preventing a liquid, fluid, or air from escaping from the engagement of output fitting 356 and the corresponding fitting or other connector.

Figure 4A:
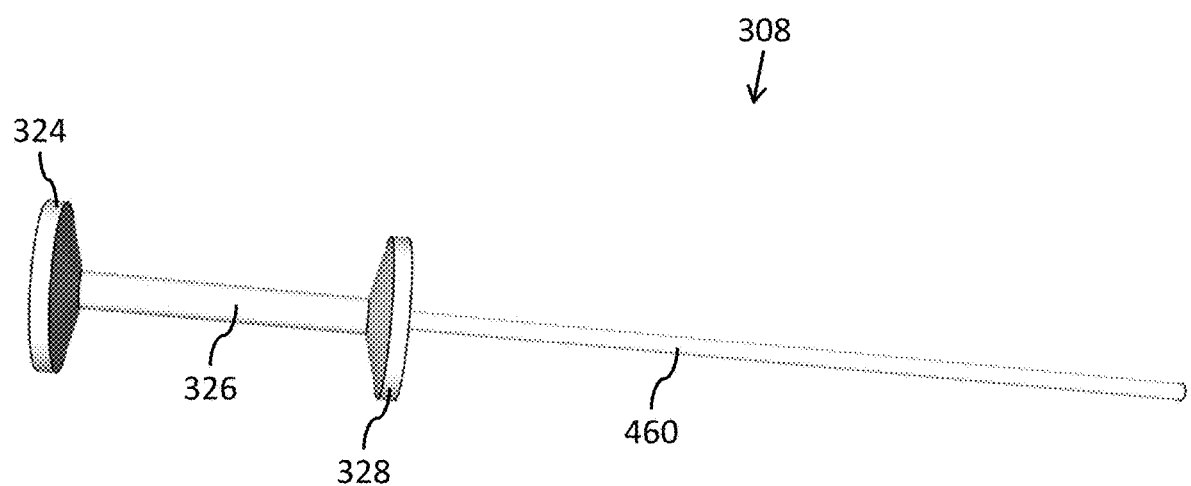
FIG. 4A is a side perspective view of a dispersed phase input needle 308.
Figure 4B:
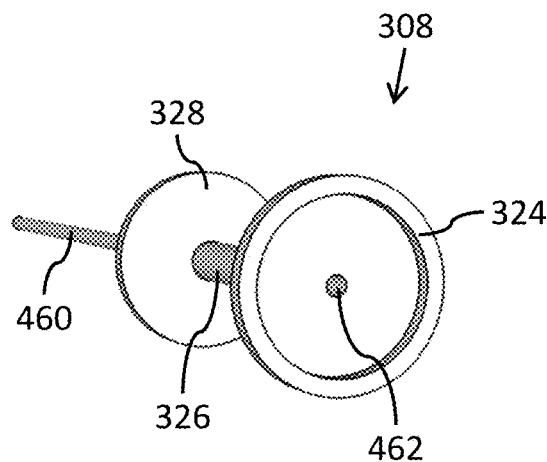
FIG. 4B is a front perspective view of dispersed phase input needle 308.
Figure 4C:
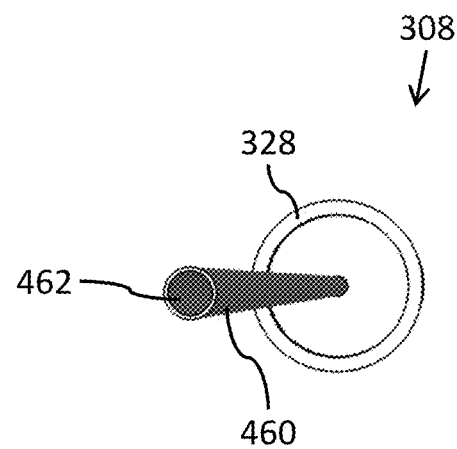
FIG. 4C is a rear perspective view of dispersed phase input needle 308.

FIGS. 4A-4C illustrate dispersed phase input needle 308. Input needle 308 is as described above with respect to FIG. 3, and includes at a second end a needle tube 460 and a bore 462 extending through the entirety of DP input needle 308. That is, bore 462 extends from DP input fitting 324 to the distal end of needle tube 460. In practice, and as described further below, the distal end of needle tube 460 is oriented within pump chamber 310 as DP flows out of the distal end of needle tube 460.

Figure 5A:
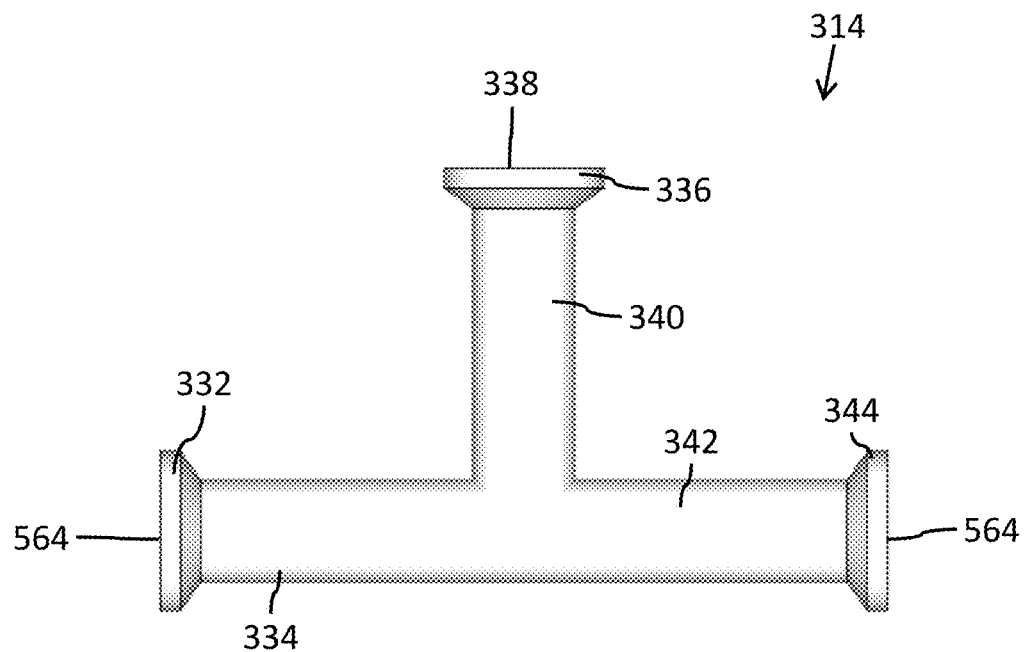
FIG. 5A is a side elevation view of a tee 314.
Figure 5B:
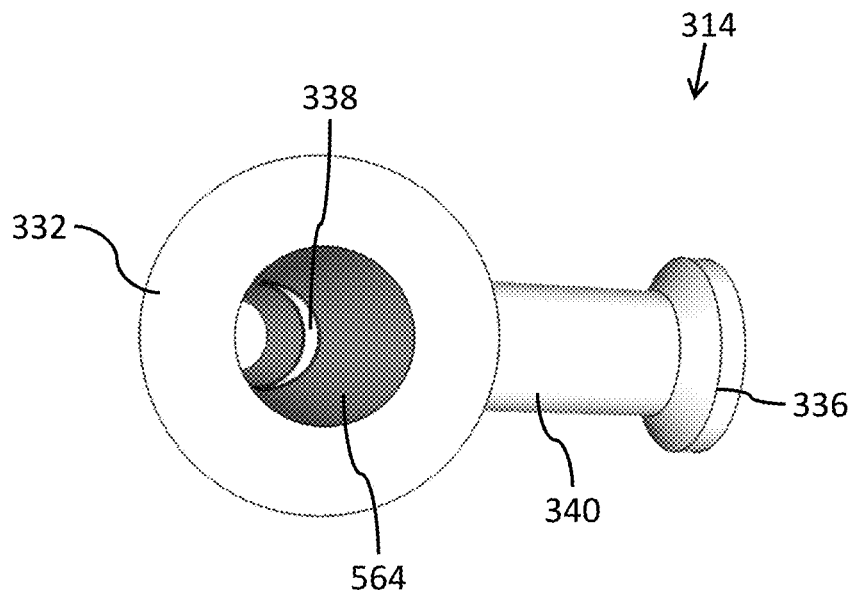
FIG. 5B is a front perspective view of tee 314.

FIGS. 5A and 5B illustrate tee 314. Tee 314 is as described above with respect to FIG. 3, and may include a hollow bore 564 extending through first tube 334 and 342. Hollow bore 564 is intersected by hollow bore 338 as illustrated in FIG. 5B. In this manner, hollow bore 338 and hollow bore 564 are fluidically connected.

Figure 6A:
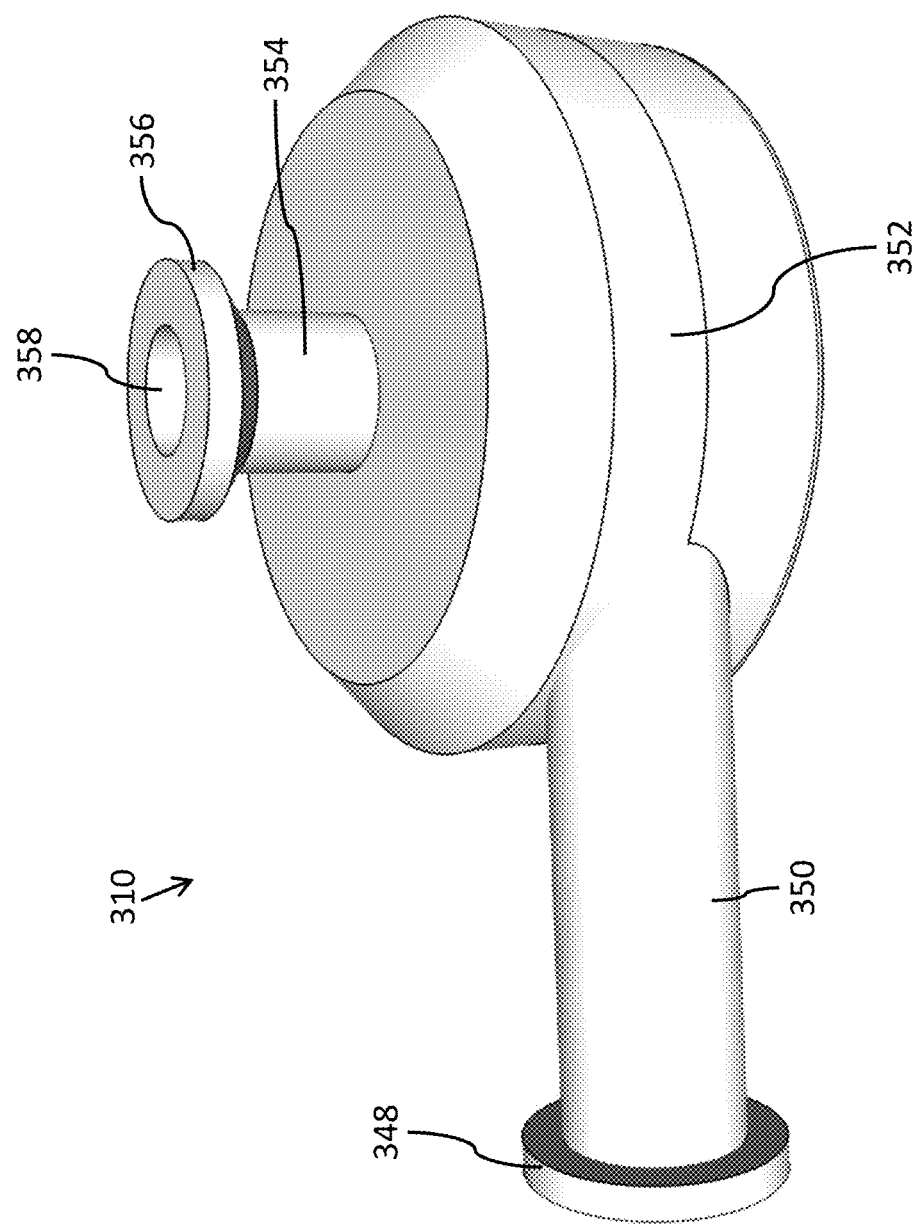
FIG. 6A is a side perspective view of a pump chamber 310.
Figure 6B:
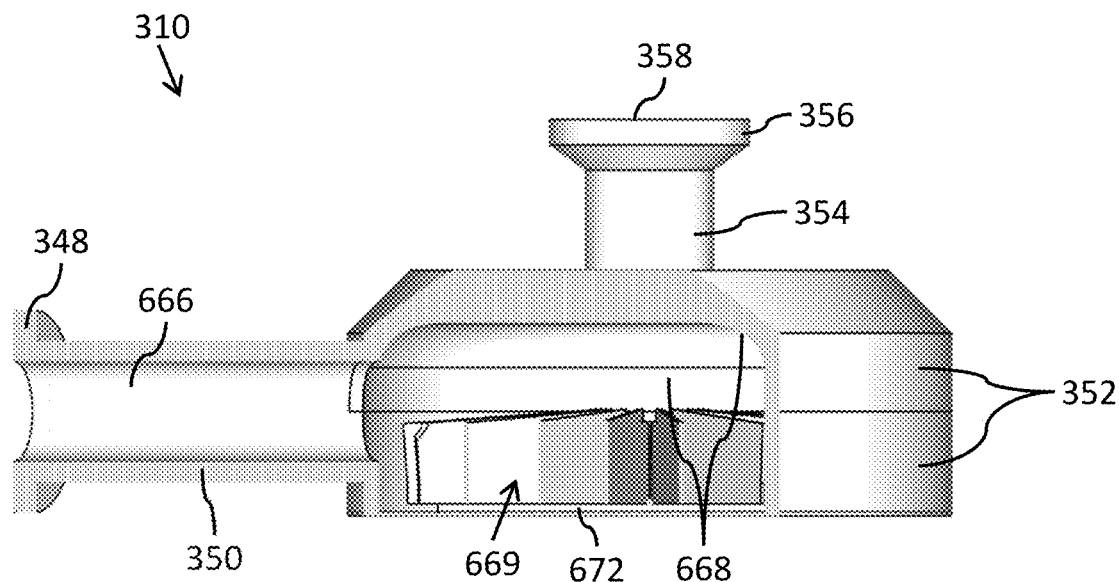
FIG. 6B is a cutaway elevation view of pump chamber 310.
Figure 6C:
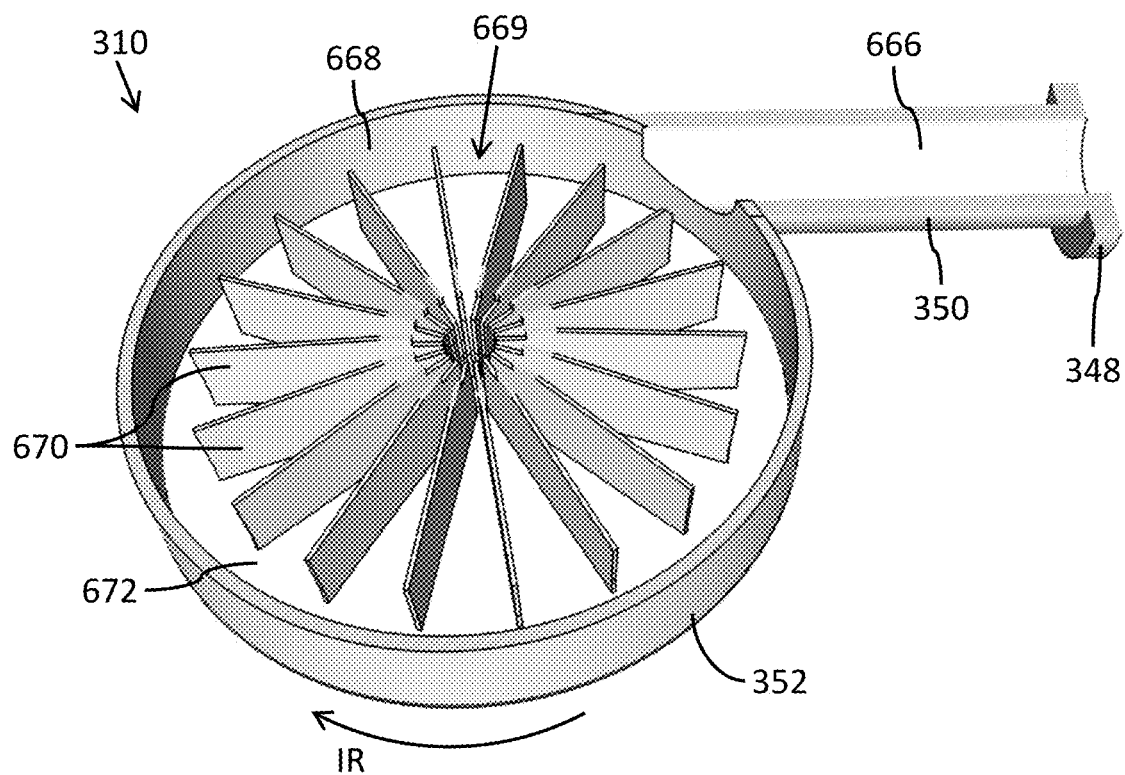
FIG. 6C is a top sectional view of pump chamber 310.

FIG. 6A-6C illustrate pump chamber 310. FIG. 6A illustrates pump chamber as described above with respect to FIG. 3. FIGS. 6B and 6C further illustrate hollow bore 666 extending through input tube 350 and input fitting 348. Hollow bore 666 extends into the hollow interior of pump chamber 310. The hollow interior is defined by interior surfaces 668. Within the hollow interior is an impeller 669 including a plurality of impeller blades 670 and a base 672.

Base 672 may include a magnet to magnetically engage a rotating magnetic field outside of pump chamber 310. The magnetic interaction between base 672 and the rotating magnetic field outside of pump chamber 310 may cause impeller 669 to levitate and rotate within the sealed pump chamber 310. Impeller 669 may rotate in the direction indicated in FIG. 6C as impeller rotation IR. Thus, impeller 669 may rotate in the direction intended by the manufacturer, but the DP an CP may be input under pressure via hollow bore 666, which was intended by the manufacturer to be the output.

Figure 7A:
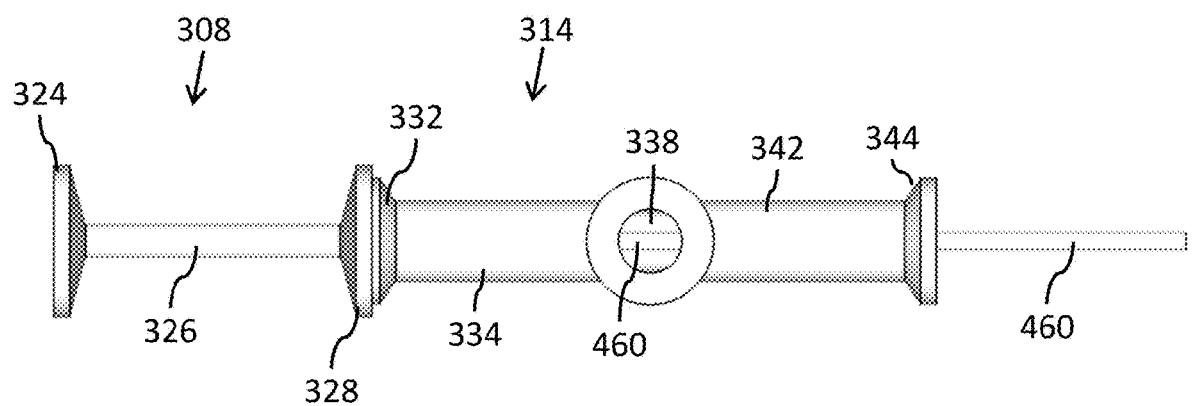
FIG. 7A is a side elevation view of a dispersed phase input needle 308 and tee 314 assembly.
Figure 7B:
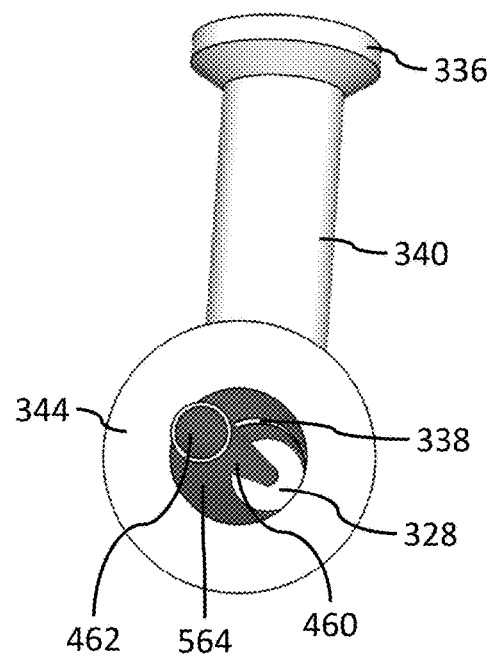
FIG. 7B is a rear elevation view of a dispersed phase input needle 308 and tee 314 assembly.

FIGS. 7A and 7B illustrate a dispersed phase input needle 308 and tee 314 assembly. DP input needle 308 and tee 314 are as they are described above with respect to FIGS. 3, 4A-4C, 5A, and 5B.

As illustrated in FIG. 7A, at least a portion of DP output fitting 328 may have a larger diameter than, and may overlap with, tee input fitting 332. Alternatively, at least a portion of DP output fitting 328 may have a smaller diameter than, and may underlap with, tee input fitting 332.

As illustrated in FIG. 7B, needle tube 460 may extend completely through tee 314.

Figure 8A:
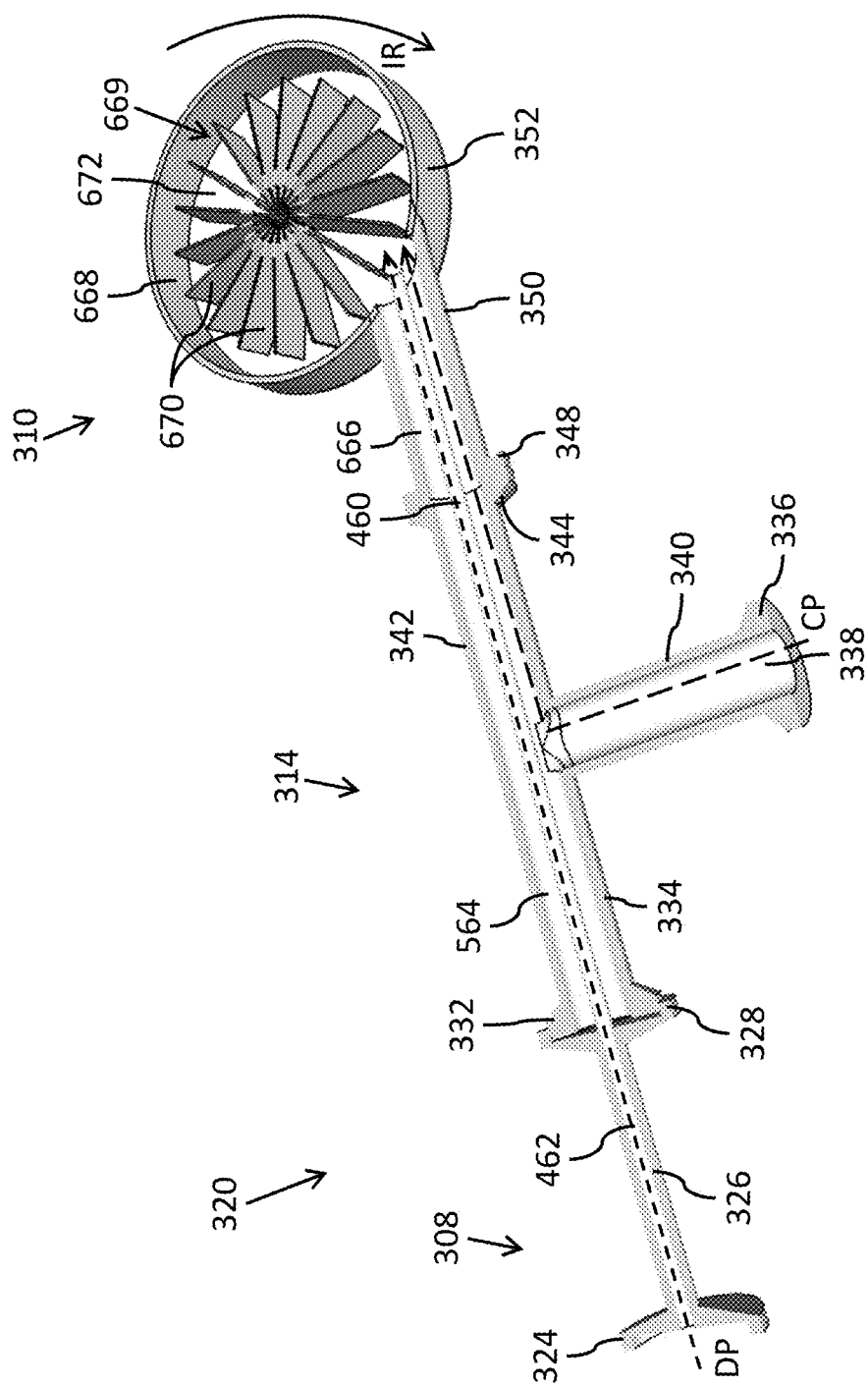
FIG. 8A is a top sectional view of microsphere formation system 320.
Figure 8B:
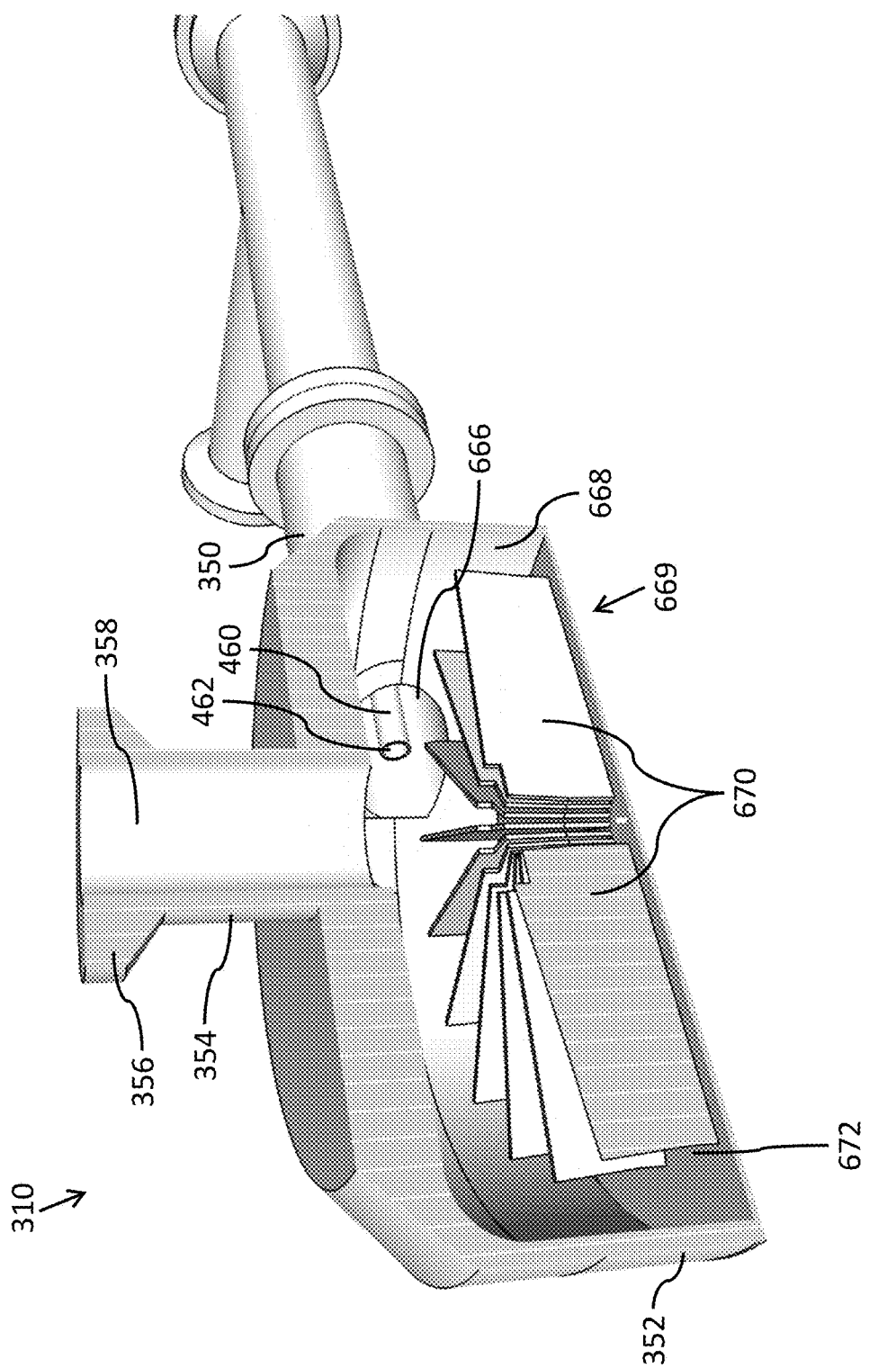
FIG. 8B is a side sectional view of microsphere formation system 320.

FIGS. 8A and 8B illustrate microsphere formation system 320. System 320 is as it and its various components are described above with respect to FIGS. 3, 4A-4C, 5A, 5B, and 6A-6C.

Needle tube 460 may extend from DP input needle 308, completely through tee 314, completely through input tube 350, and into the hollow interior of pump chamber 310. Needle tube 460 may terminate adjacent to, and within the immediate vicinity of the outer diameter of the circle traced by the radially out edges of impeller blades 670 when impeller 669 rotates, such that needle tube 460 discharges DP into the immediate vicinity of impeller blades 670, without interfering with the rotation of impeller 669. Needle tube 460 may terminate within 1.0 mm, 2.0 mm, 3.0 mm, 4.0 mm, 5.0 mm, 6.0 mm, 7.0 mm, 8.0 mm, 9.0 mm, or 10.0 mm of the circle traced by the radially outermost portion of impeller blades 670 when impeller 669 rotates. Needle tube 460 may terminate less than 1.0 mm, 2.0 mm, 3.0 mm, 4.0 mm, 5.0 mm, 6.0 mm, 7.0 mm, 8.0 mm, 9.0 mm, or 10.0 mm of the circle traced by the radially outermost portion of impeller blades 670 when impeller 669 rotates.

As illustrated in FIG. 8A, DP (illustrated by a dashed line) enters bore 462 of DP needle 308 at or near DP input fitting 324, and extends along the length of needle tube 460 to be discharged within the hollow interior of pump chamber 310. CP (illustrated by a dashed line) enters bore 338 of tee 314 at or near CP input fitting 336, and travels to bore 564 within bore 564 but outside of needle tube 460, travels through bore 666 but outside of needle tube 460, and into the hollow interior of pump chamber 310. In this manner, CP and DP do not come into contact with one another until both are inside of pump chamber 310, and in the vicinity of impeller 669 where DP is discharged.

CP and DP are subjected to a high-shear environment within pump chamber 310 to form microspheres, and the mixture of CP and DP (including microspheres) exits pump chamber 310 via bore 358, where the mixture proceeds to a vessel, filter, static mixer, or pump.

FIG. 8B further illustrates the termination of needle tube 460, and thus the discharge of DP, in the immediate vicinity of impeller 669 blades 670. At this point, DP and CP are allowed to meet and mix, while the high-shear environment created by impeller 669 creates microspheres.

Figure 9A:
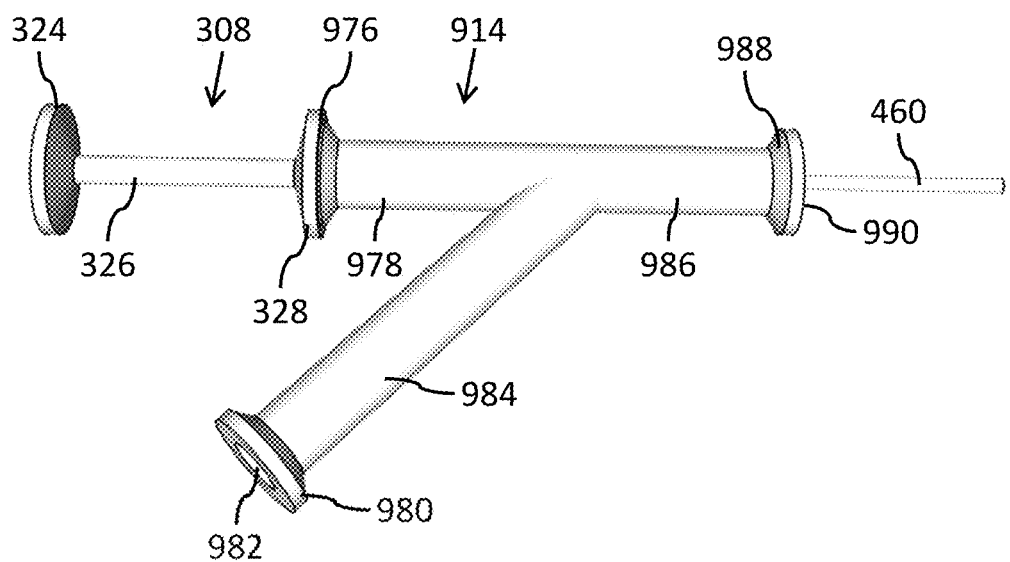
FIG. 9A is a top plan view of a dispersed phase input needle 308 and wye 914 assembly.
Figure 9B:
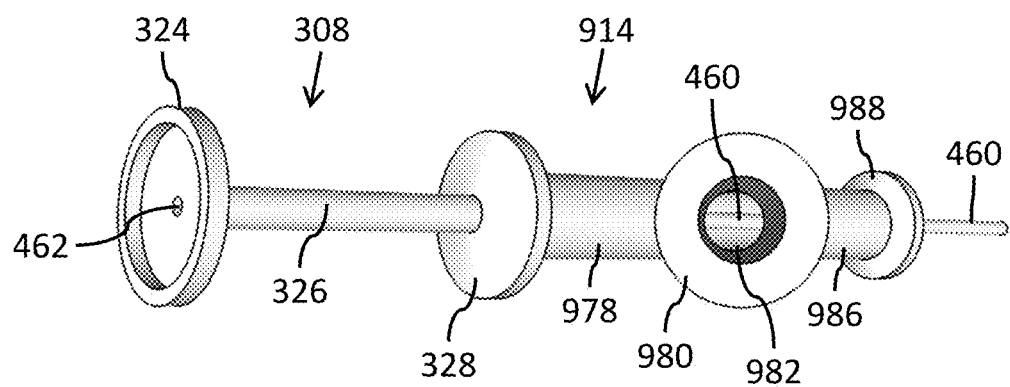
FIG. 9B is a side elevation view of a dispersed phase input needle 308 and wye 914 assembly.

FIGS. 9A and 9B illustrate a dispersed phase input needle 308 and wye 914 assembly. DP input needle 308 is as it is described above. However, tee 314 is replaced with wye 914.

It is understood that wye 914 is substantially similar to tee 314 in function, with the exception of its shape. Wye 914 may be formed of any of a variety of materials, including for example a metal (e.g., stainless steel) or a polymer. Wye 914 may be used in lieu of tee 314 where less turbulent flow of CP is desired and/or where higher pressure of CP is used.

Wye 914 may include a generally Y-shaped member formed from three tubes (first tube 978, second tube 984, and third tube 986). First tube 978 and third tube 986 may be coaxial in arrangement. First tube 978 and third tube 986 may actually be different ends of the same tube, and second tube 984 may simply butt into the combined first and third tube. A wye input fitting 976 may be connected to a first end of first tube 978. A CP input fitting 980 may be connected to a first end of second tube 984. A CP output fitting 988 may be connected to a first end of third tube 986. First tube 978, second tube 984, and third tube 986 may be connected to one another at their second ends, or alternatively, where first tube 978 and third tube 986 are actually different ends of the same tube, the combined first/third tube is connected to second tube 984 at the second end of second tube 984, at a location somewhere along the length of the combined first/third tube. Each of the tubes may include a hollow bore, and each of the hollow bores may be in fluid communication with one another. Second tube 984 includes a hollow bore 982. First tube 978 and third tube 986, being coaxial, may share a bore 990.

Needle tube 460 may extend completely through wye 914.

Figure 10:
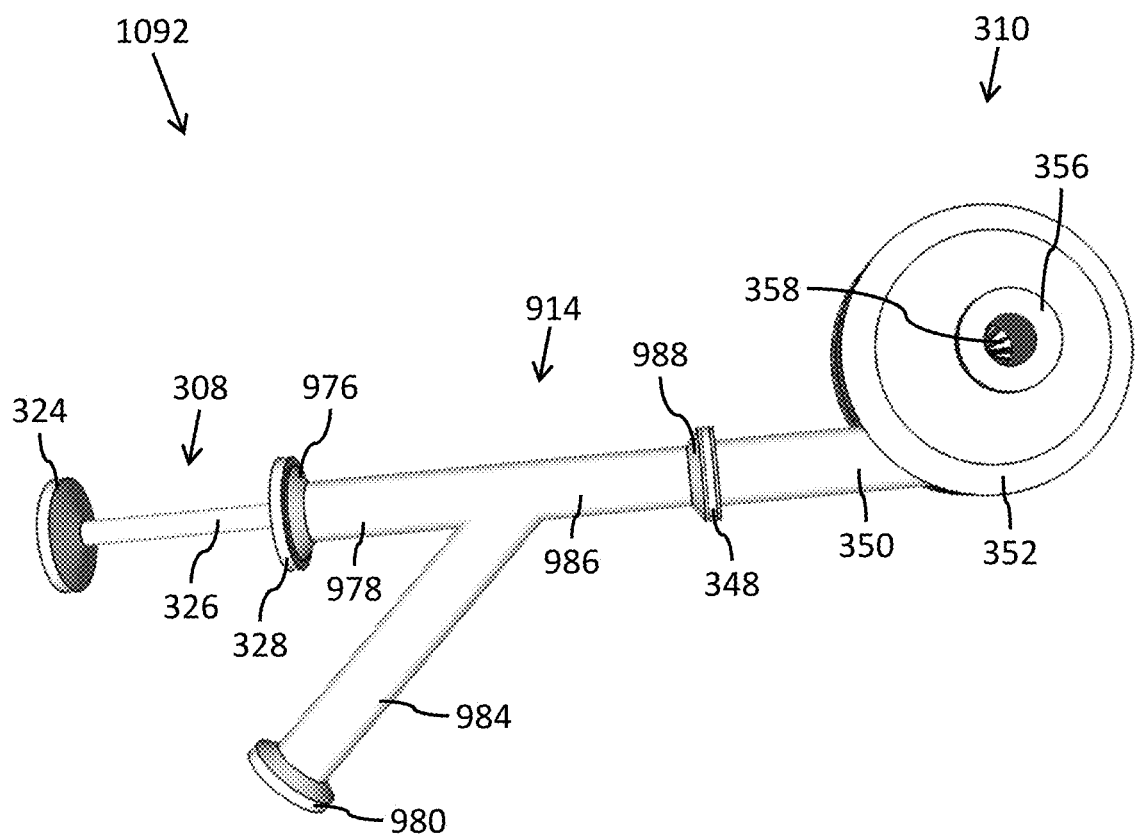
FIG. 10 is a perspective view of a microsphere formation system 1092.

FIG. 10 is a microsphere formation system 1092. System 1092 may include a DP needle 308, a wye 914, and a pump chamber 310. DP needle 308 and pump chamber 310 are as they were described above with respect to FIG. 3 and system 320.

Wye 914 may include a generally Y-shaped member formed from three tubes (first tube 978, second tube 984, and third tube 986). A wye input fitting 976 may be connected to a first end of first tube 978, and may engage DP output fitting 328 to create a seal to prevent the leaking of a liquid, fluid, or air from the engagement of fitting 976 and fitting 328.

A CP input fitting 980 may be connected to a first end of second tube 984. A CP output fitting 988 may be connected to a first end of third tube 986. CP input fitting 980 may engage a corresponding fitting or other connector from a supply line or CP pump to create a seal preventing a liquid, fluid, or air from escaping from the engagement of CP input fitting 980 with the corresponding fitting or other connector. In practice, CP is positively pressurized by a CP pump, causing CP to flow into wye 914 at input fitting 980, through bore 982, through bore 990, and flow out of wye 914 at CP output fitting 988. CP cannot flow out of wye 914 at wye input fitting 976 due to the seal created between wye input fitting 976 and DP output fitting 328. CP output fitting 988 may engage input fitting 348 of pump chamber 310 to create a seal to prevent the leaking of a liquid, fluid, or air form the engagement of fitting 988 fitting 348.

For any of the aforementioned systems, including system 320 and 1092, the flow rate of the DP through DP needle 308 into pump chamber 310 may be 5-500 mL per minute; or more commonly 10-50 mL per minute. The flow rate may be approximately 30 mL per minute. Where the system is used to create an emulsion, the flow rate could exceed 500 mL per minute.

For any of the aforementioned systems, including system 320 and 1092, the flow rate of the CP through tee 314 or wye 914 into the pump chamber 310 may be 0.5-40 L per minute; or more commonly 1.0-4.0 L per minute. The flow rate of CP may be approximately 2.0 L per minute.

For any of the aforementioned systems, including system 320 and 1092, the ratio of the amount of CP:DP directed to pump chamber 310 may range between 5:1-80:1. For any of the aforementioned systems, including system 320 and 1092, the ratio of the amount of CP:DP directed to pump chamber 310 may range between 1:1-80:1. For any of the aforementioned systems, including system 320 and 1092, the ratio of the amount of CP:DP directed to pump chamber 310 may range between 5:1-160:1. For any of the aforementioned systems, including system 320 and 1092, the ratio of the amount of CP:DP directed to pump chamber 310 may range between 1:1-160:1. For any of the aforementioned systems, including system 320 and 1092, the ratio of the amount of CP:DP directed to pump chamber 310 may range between 160:1-1:80. The ratio of an inner aqueous phase (which may be CP):DP may be smaller for the creation of emulsions compared to that ratio for the creation of microspheres, including for example 1:1-1:80.

Various impeller rotational speeds may be used depending on the size of microspheres desired. In general, higher impeller rotational speeds will typically result in smaller microspheres. For example, the speed of impeller 669 may range between 1,000 RPM and 4,500 RPM. Alternatively, the speed of impeller 669 may be as large as 6,000 RPM. Alternatively, the speed of impeller 669 may be as large as 9,000 RPM.

For any of the aforementioned systems, including system 320 and 1092, drug loads may range between 3.4% and 62.0%. In another aspect, for any of the aforementioned systems, including system 320 and 1092, drug loads may range between 0.01% and 75.0%. For any of the aforementioned systems, including system 320 and 1092, encapsulation efficiency may range between 34.0% and 97.0%. For any of the aforementioned systems, including system 320 and 1092, encapsulation efficiency may range between 1.0% and 99.0%. For any of the aforementioned systems, including system 320 and 1092, d10 (μm) may range between 6.5 and 58.0; d50 (μm) may range between 14.7 and 192.0; and d90 (μm) may range between 24.6 and 462.0. For any of the aforementioned systems, including system 320 and 1092, d10 (μm) may be as small as 0.5. In one aspect, d10 is the diameter where 10% of the distribution has a particle size smaller than the indicated diameter, whereas 90% of the distribution has a particle size larger than the indicated diameter. In one aspect, d50 is the diameter where 50% of the distribution has a particle size smaller than the indicated diameter, whereas 50% of the distribution has a particle size larger than the indicated diameter. In one aspect, d90 is the diameter where 90% of the distribution has a particle size smaller than the indicated diameter, whereas 10% of the distribution has a particle size larger than the indicated diameter.

Optionally, the resulting microspheres may undergo a washing step. This will depend on the end use of the microspheres, as well as depending on what solvents have been used in the process. Residual solvents that might be harmful to a patient to which the microspheres will be administered should preferably be washed so as to limit the amount of, or effectively eliminate, such solvents that are in the finished dosage form. The washing may also rid the solution of surfactants used within the CP.

The microspheres may also be dried. A drying step may be carried out using a variety of commercially available drying equipment commonly used in pharmaceutical dosage form manufacturing. In another embodiment, the drying step may be carried out by lyophilization.

Microspheres formed by the present invention may be microspheres that encapsulate a drug substance, or may be matrix microspheres where the drug substance is dispersed throughout the microsphere. Placebo microspheres can also be produced by the described system and method. Other types of microspheres, particularly for pharmaceutical use, are envisioned within the scope of the described system and method.

Any drug for which controlled or extended release is advantageous or useful may be used in the methods of the present disclosure. For example, antidepressants, antianxiety drugs, pain medications and anti-inflammatory drugs, chemotherapy or other anti-cancer medications, contraceptives, hormones, drugs used to treat disorders such as Attention Deficit Disorder or Attention Deficit and Hyperactivity Disorder, antihistamines and other drugs used by allergy sufferers, and antacids and other drugs that treat various gastrointestinal issues. As noted, this list is non-exhaustive, as there are a wide variety of drug classes that have been or are currently used in controlled or extended release forms that could be used in a microsphere controlled or extended release form, and that likewise, compounds may be developed in the future that similarly could be incorporated into microspheres.

Figure 11A:
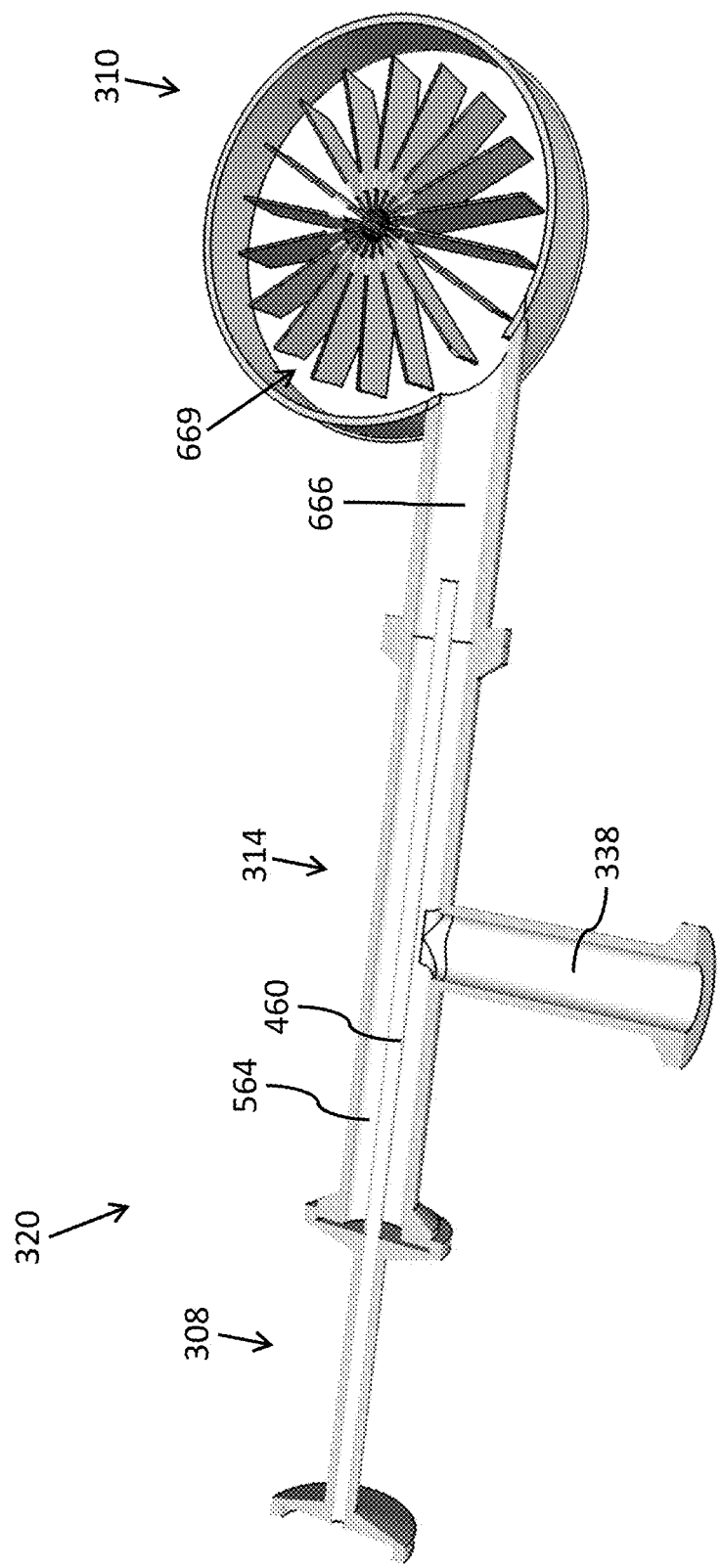
FIG. 11A is a top sectional view of microsphere formation system 320.

FIG. 11A is a microsphere formation system 320. System 320 may include a DP needle 308, a tee 314, and a pump chamber 310.

DP needle 308 may include a needle tube 460. Tee 314 may include a hollow linear bore 564 and a hollow perpendicular bore 338. Chamber 310 may include an input tube having a bore 666. An impeller 669 may be contained within chamber 310.

Needle tube 460 may terminate within bore 666 but not in the immediate vicinity of impeller 669.

Figure 11B:
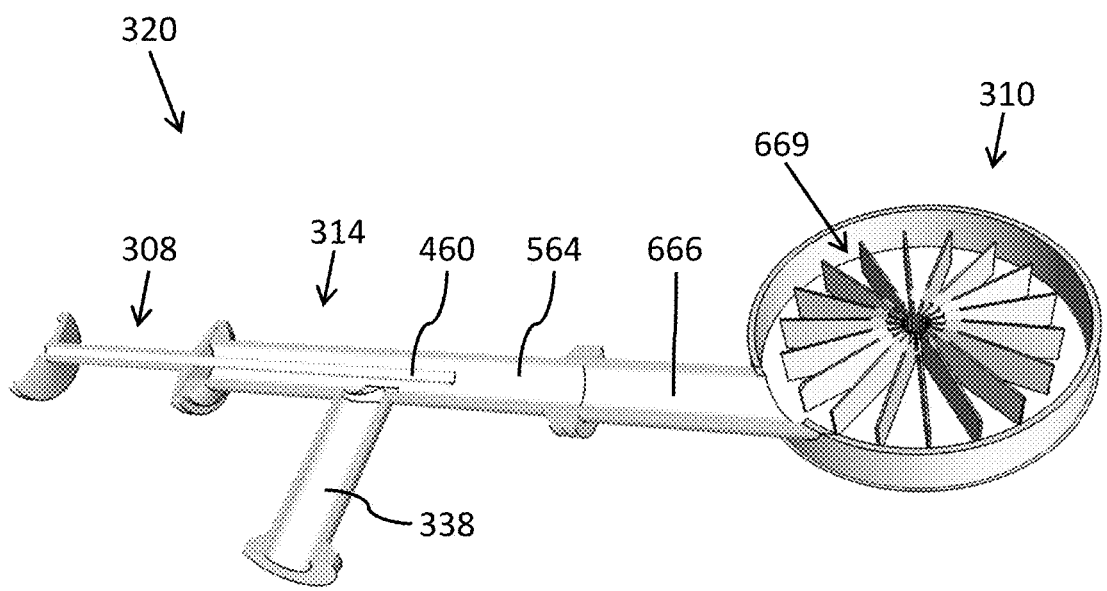
FIG. 11B is a top sectional view of microsphere formation system 320.

FIG. 11B is a microsphere formation system 320. Needle tube 460 may terminate within bore 564 of tee 314. Needle tube 460 may terminate at a point between the junction of bores 564 and 338, and chamber 310.

Figure 11C:
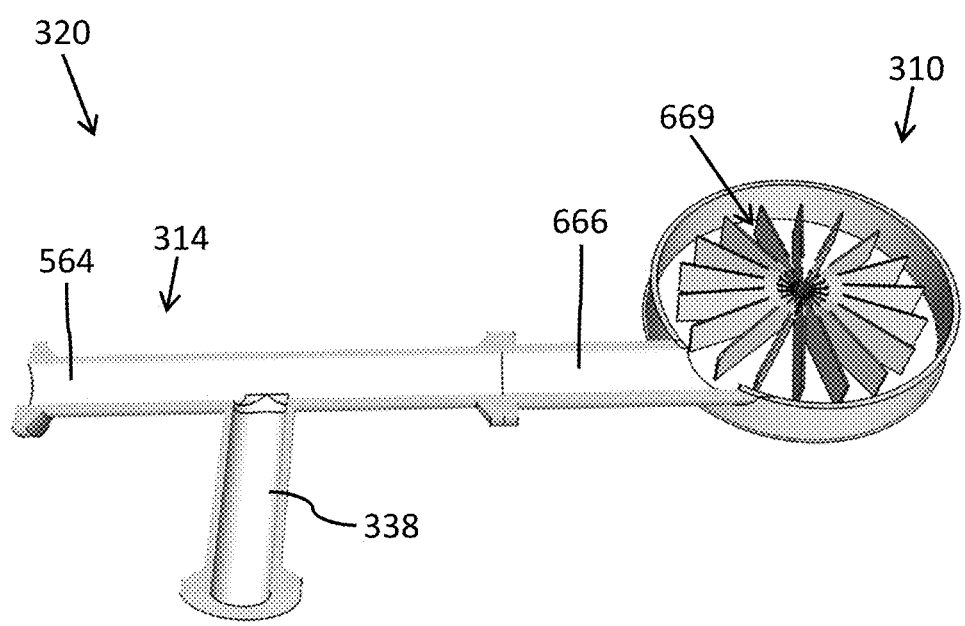
FIG. 11C is a top sectional view of microsphere formation system 320.
Figure 12A:
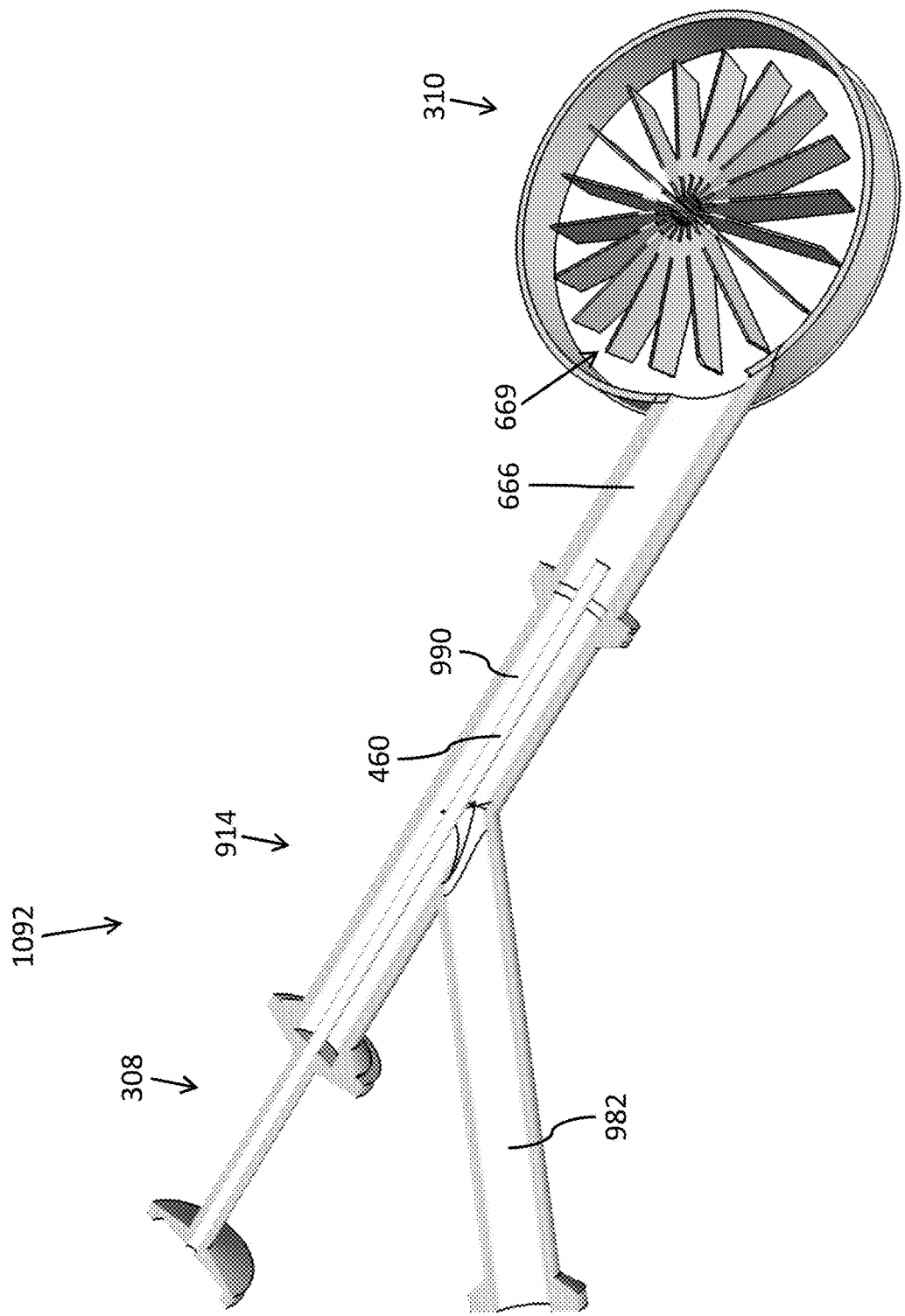
FIG. 12A is a top sectional view of microsphere formation system 1092.
Figure 12B:
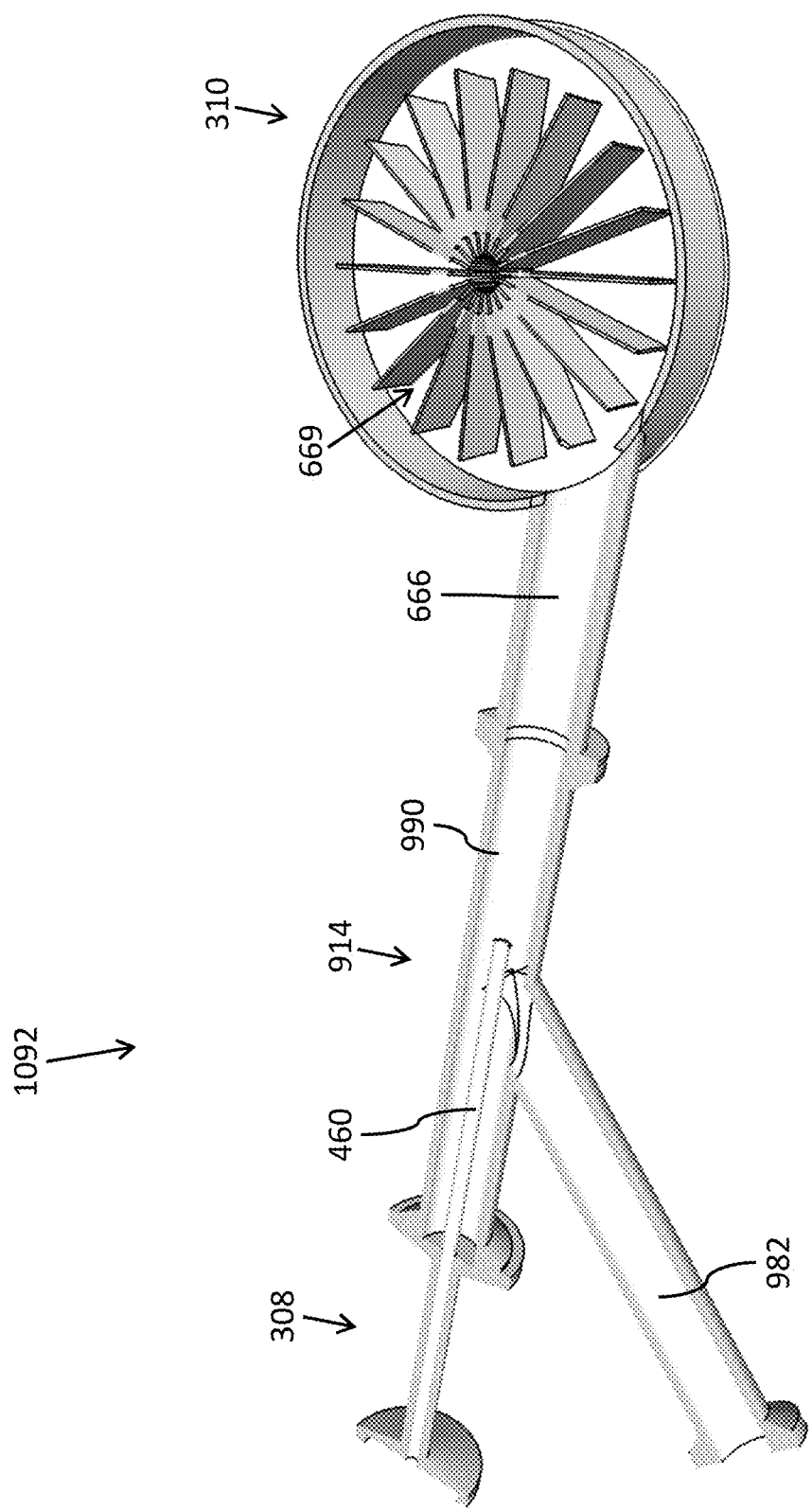
FIG. 12B is a top sectional view of microsphere formation system 1092.
Figure 12C:
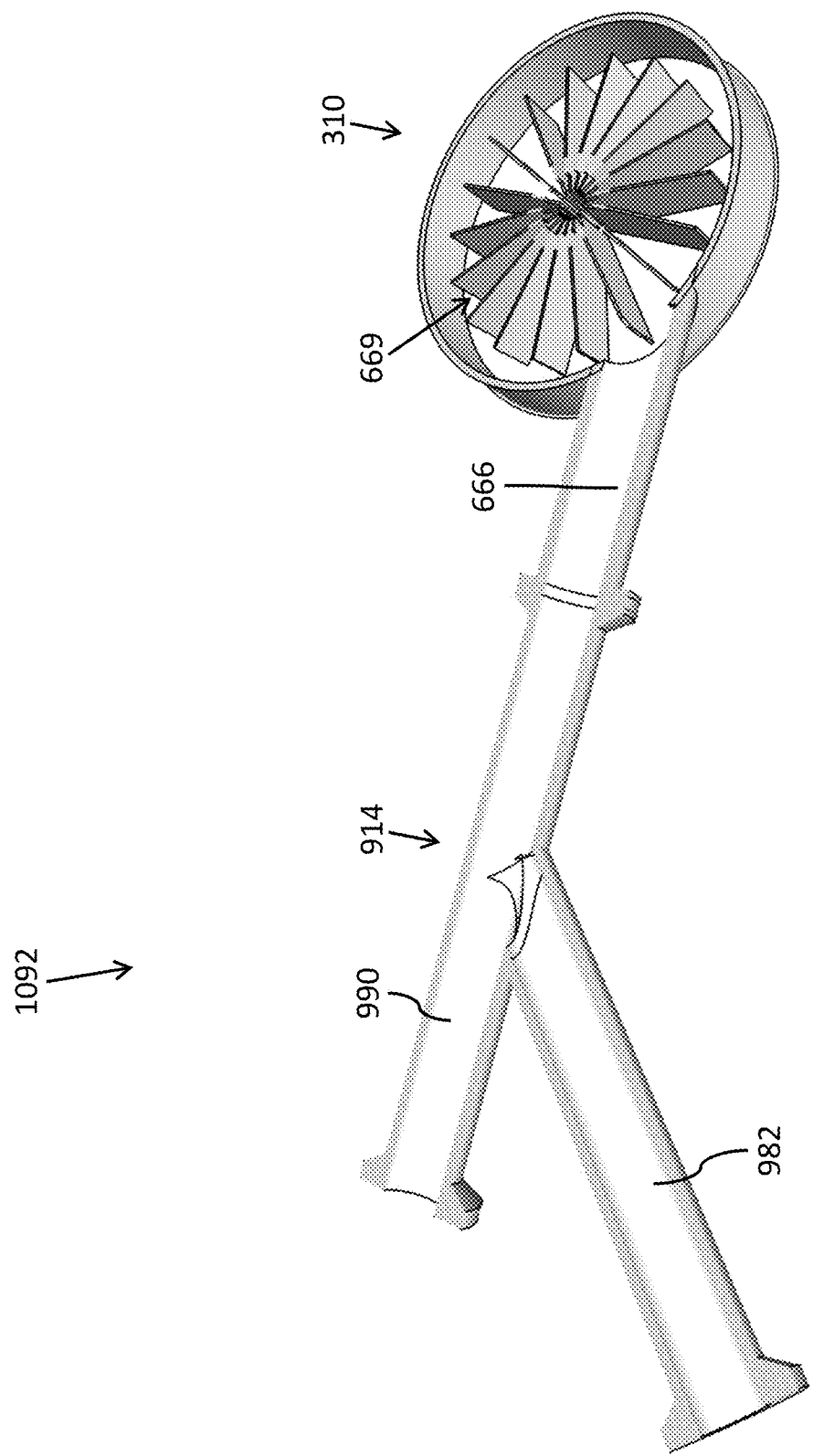
FIG. 12C is a top sectional view of microsphere formation system 1092.

FIG. 11C is a microsphere formation system 320. This arrangement of system 320 may be completely devoid of DP needle 308 and needle tube 460. In such an embodiment, DP and CP are directly fed into tee 314 at either of the two open ends illustrated in FIG. 11C (e.g., to flow into bore 564 or bore 338). In one arrangement, DP is directed into bore 564 and CP is directed into bore 338, and the two mix within tee 314 and travel under positive pressure into bore 666 and the interior of pump chamber 310, where the two interact with impeller 669. Alternatively, DP may be directed into bore 338, while CP is directed into bore 564, and the two mix within tee 314 and travel under positive pressure to interact with impeller 669.

FIG. 12A is a microsphere formation system 1092. System 1092 may include a DP needle 308, a wye 914, and a pump chamber 310.

DP needle 308 may include a needle tube 460. Wye 914 may include a hollow linear bore 990 and a hollow angled bore 982. Chamber 310 may include an input tube having a bore 666. An impeller 669 may be contained within chamber 310.

Needle tube 460 may terminate within bore 666 but not in the immediate vicinity of impeller 669.

FIG. 12B is a microsphere formation system 1092. Needle tube 460 may terminate within bore 990 of wye 914. Needle tube 460 may terminate at a point between the junction of bores 990 and 982, and chamber 310.

FIG. 12C is a microsphere formation system 1092. This arrangement of system 1092 may be completely devoid of DP needle 308 and needle tube 460. In such an embodiment, DP and CP are directly fed into wye 914 at either of the two open ends illustrated in FIG. 12C (e.g., to flow into bore 990 or bore 982). In one arrangement, DP is directed into bore 990 and CP is directed into bore 982, and the two mix within wye 914 and travel under positive pressure into bore 666 and the interior of pump chamber 310, where the two interact with impeller 669. Alternatively, DP may be directed into bore 982, while CP is directed into bore 990, and the two mix within wye 914 and travel under positive pressure to interact with impeller 669.

Figure 13A:
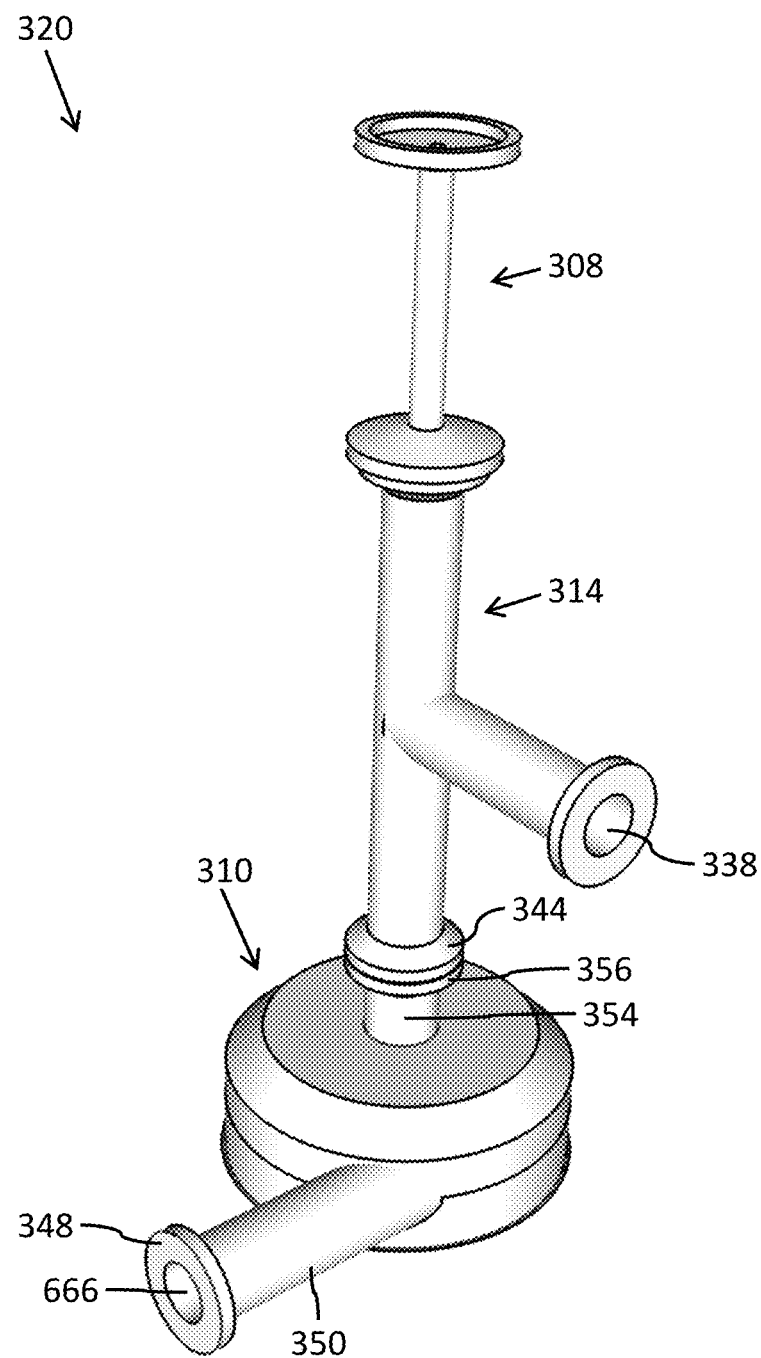
FIG. 13A is a perspective view of an alternative arrangement of microsphere formation system 320.

FIG. 13A illustrates an alternative arrangement of system 320, including a DP needle 308, a tee 314, and a pump chamber 310. In this arrangement, tee 314 and DP needle 308 input the CP and DP into the intended input (output tube 354) of pump chamber 310 (that is, the input as intended by the manufacturer), and the mixture is removed via the intended output (input tube 350) of pump chamber 310 (that is, the output as intended by the manufacturer). In this configuration, the DP and CP mix within chamber 310 in a low shear environment in a flow direction as intended by the manufacturer. However, microspheres and/or an emulsion may still be formed in such an arrangement.

Specifically, CP output fitting 344 may engage output fitting 356 of output tube 354. DP may be injected into the system via DP needle 308, while CP is introduced to the system via bore 338.

Figure 13B:
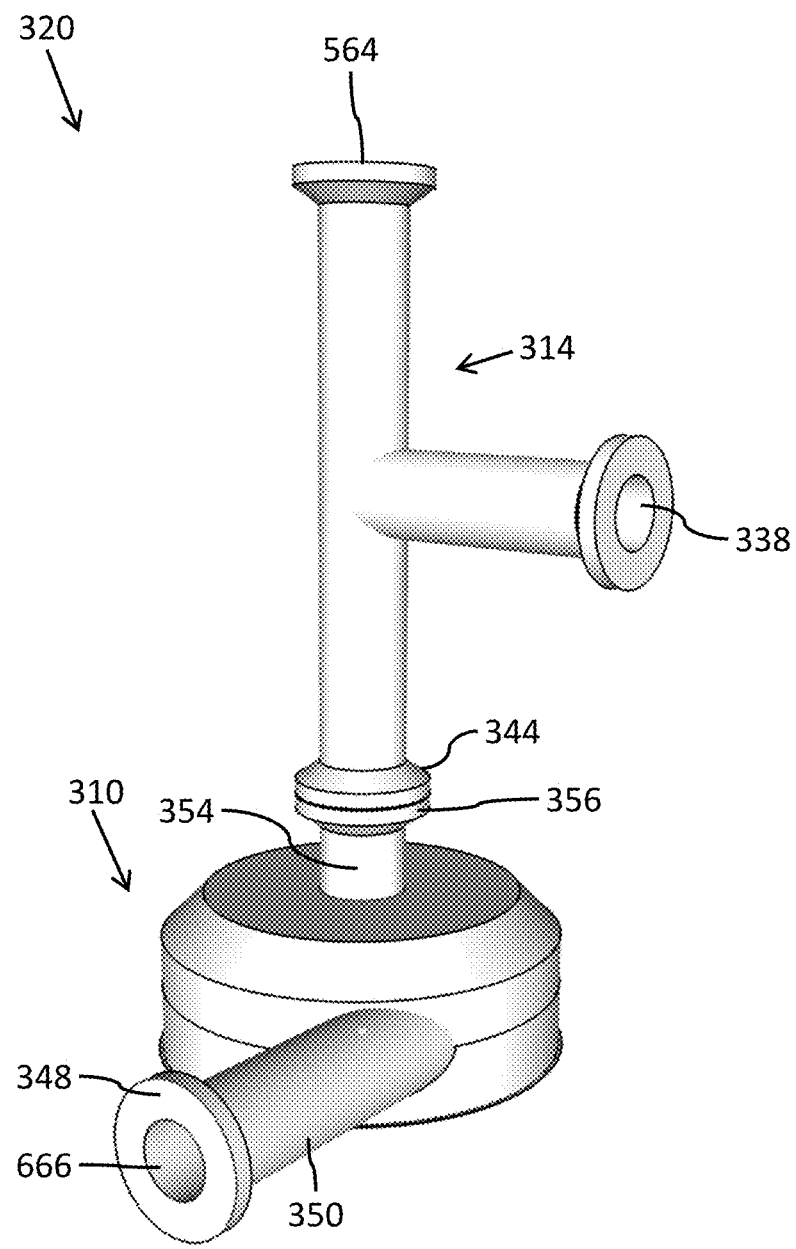
FIG. 13B is a perspective view of an alternative arrangement of microsphere formation system 320.

FIG. 13B illustrates an alternative arrangement of system 320 that is substantially similar to that arrangement illustrated in FIG. 13A, but where system 320 is devoid of DP needle 308 altogether, and DP and CP are introduced through one of bore 564 and 338, to mix within tee 314 and proceed into outlet tube 354.

Figure 14A:
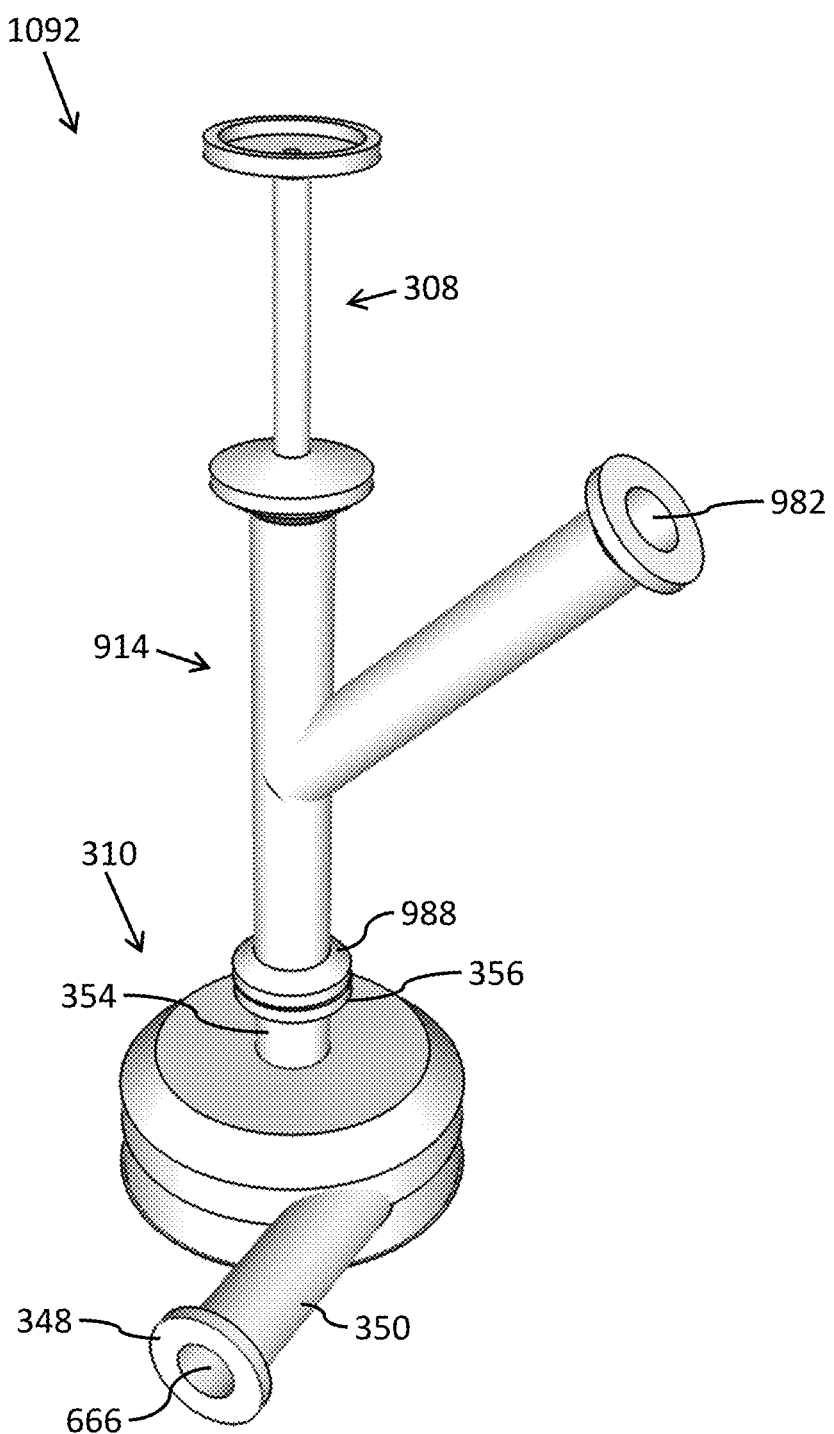
FIG. 14A is a perspective view of an alternative arrangement of microsphere formation system 1092.

FIG. 14A illustrates an alternative arrangement of system 1020, including a DP needle 308, a wye 914, and a pump chamber 310. In this arrangement, wye 914 and DP needle 308 input the CP and DP into the intended input (output tube 354) of pump chamber 310 (that is, the input as intended by the manufacturer), and the mixture is removed via the intended output (input tube 350) of pump chamber 310 (that is, the output as intended by the manufacturer). In this configuration, the DP and CP mix within chamber 310 in a low shear environment in a flow direction as intended by the manufacturer. However, microspheres and/or an emulsion may still be formed in such an arrangement.

Specifically, CP output fitting 988 may engage output fitting 356 of output tube 354. DP may be injected into the system via DP needle 308, while CP is introduced to the system via bore 990.

Figure 14B:
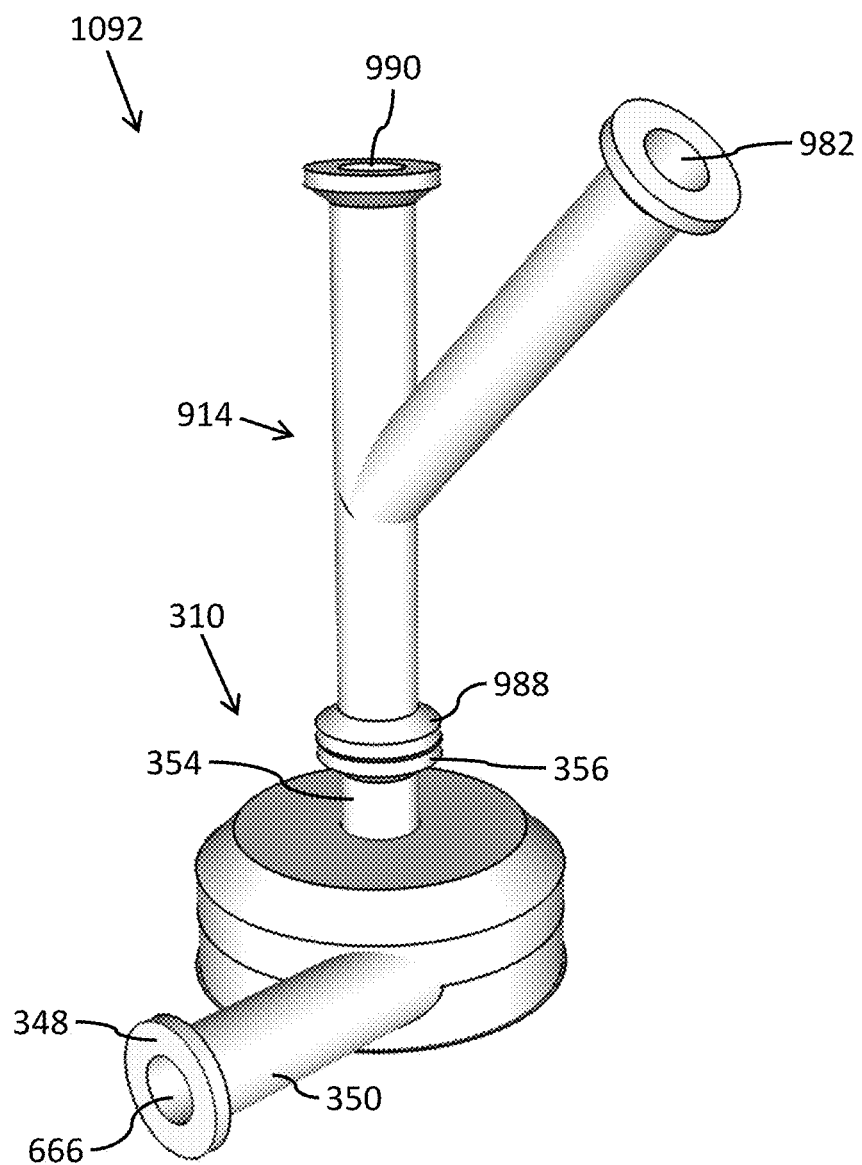
FIG. 14B is a perspective view of an alternative arrangement of microsphere formation system 1092.

FIG. 14B illustrates an alternative arrangement of system 1092 that is substantially similar to that arrangement illustrated in FIG. 14A, but where system 1092 is devoid of DP needle 308 altogether, and DP and CP are introduced through one of bore 990 and 982, to mix within wye 914 and proceed into outlet tube 354.

Figure 15:
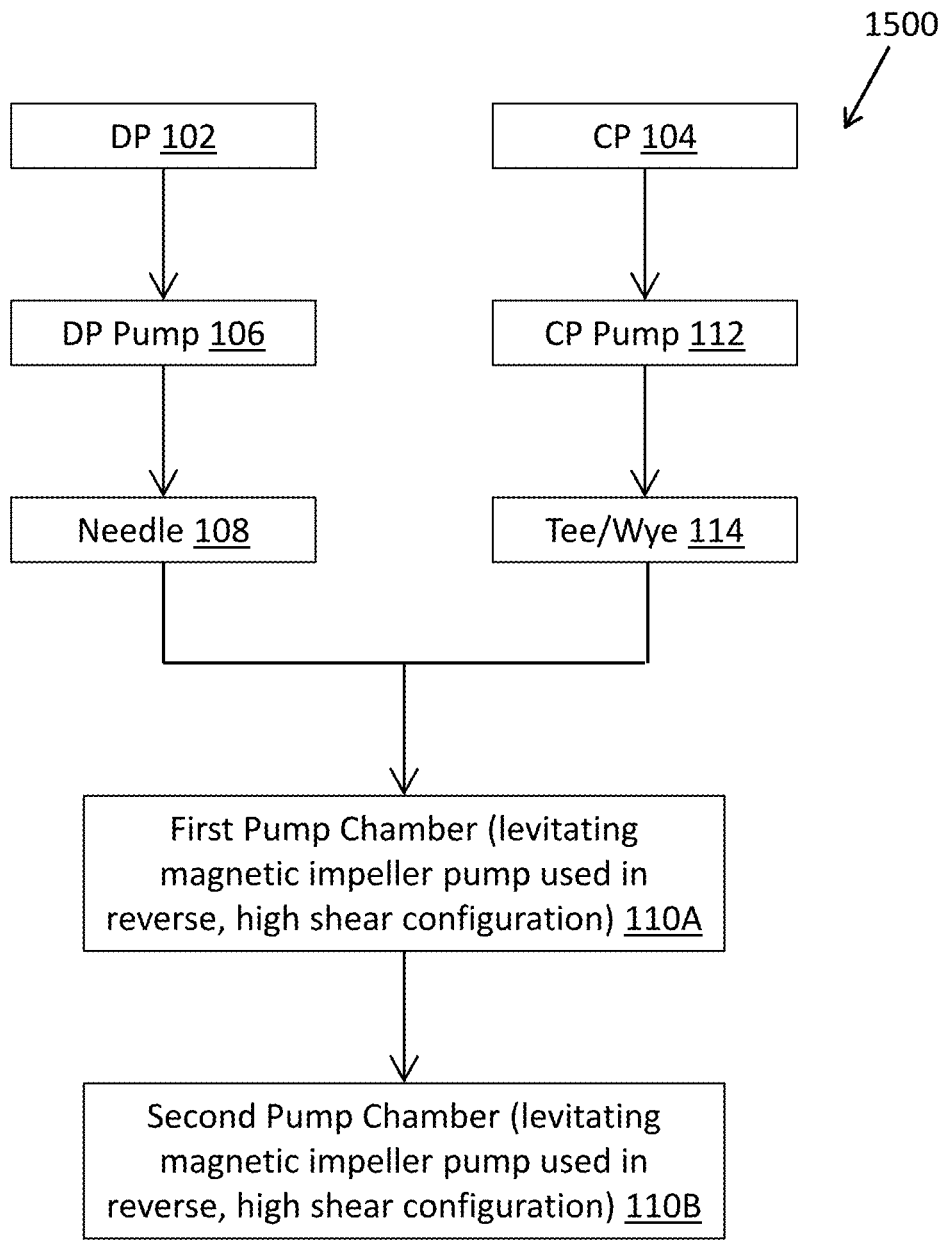
FIG. 15 is a schematic illustrating a system 1500 for producing microspheres.

FIG. 15 is a schematic illustrating a system 1500 for producing microspheres. System 1500 may include a DP source 102 (e.g., a reservoir) operatively connected to a DP pump 106 configured to positively pressurize DP to force DP through a DP needle 108 and into a first pump chamber 110A of a levitating magnetic impeller pump, operated in reverse of its intended configuration to create a high shear homogenizer. System 1500 may include a CP source (e.g., a reservoir) operatively connected to a CP pump 112 configured to positively pressurize CP to force CP through a tee/wye 114 and into first pump chamber 110A. The contents of first pump chamber 110A is pumped into a second pump chamber 110B operated in reverse of its intended configuration to create a high shear homogenizer, following homogenization of the solution within first pump chamber 110A.

Figure 16:
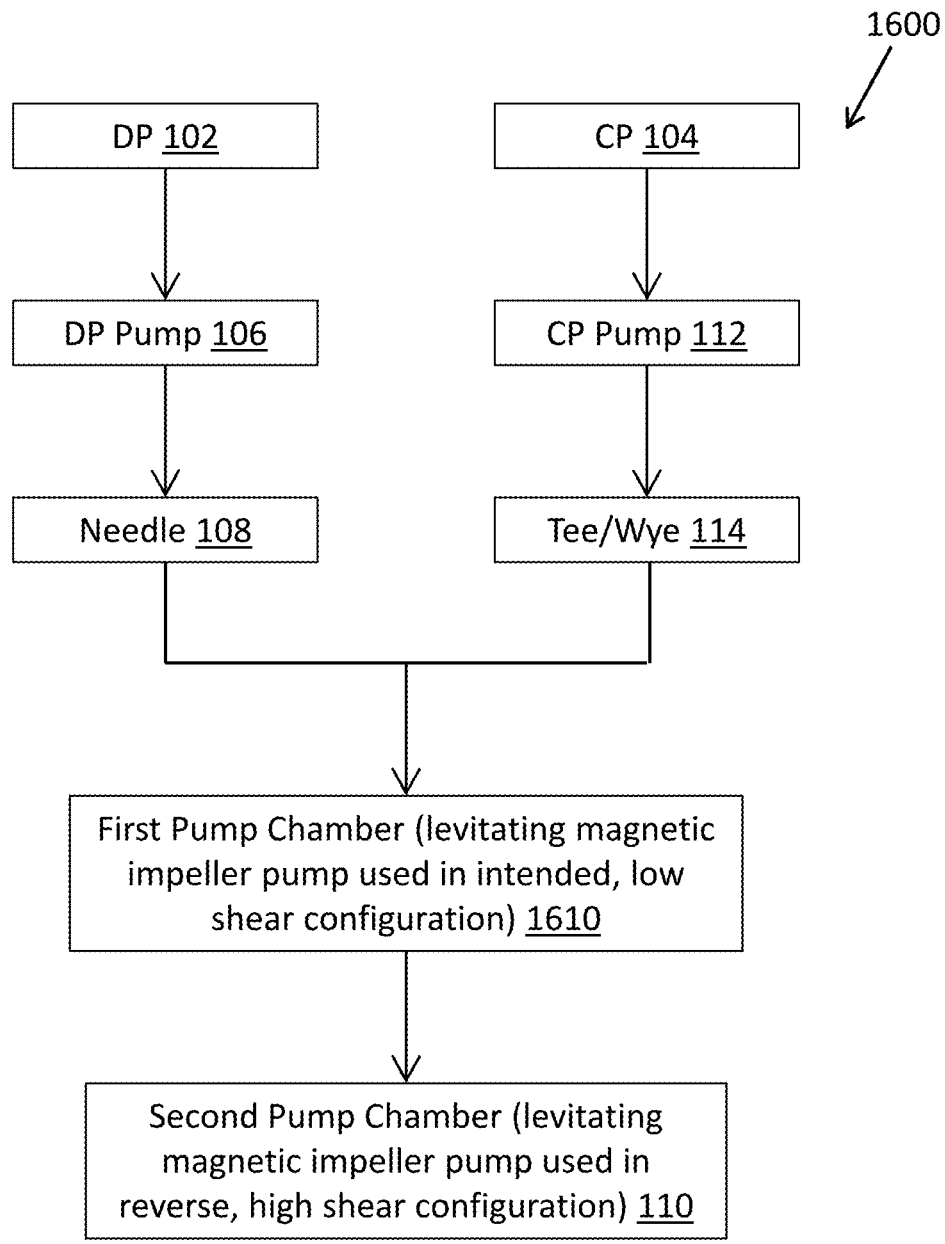
FIG. 16 is a schematic illustrating a system 1600 for producing microspheres.

FIG. 16 is a schematic illustrating a system 1600 for producing microspheres. System 1600 may include a DP source 102 (e.g., a reservoir) operatively connected to a DP pump 106 configured to positively pressurize DP to force DP through a DP needle 108 and into a first pump chamber 1610 of a levitating magnetic impeller pump operated in its intended configuration to create a low shear pump. System 1600 may include a CP source (e.g., a reservoir) operatively connected to a CP pump 112 configured to positively pressurize CP to force CP through a tee/wye 114 and into first pump chamber 1610. The contents of first pump chamber 1610 is pumped into a second pump chamber 110 operated in reverse of its intended configuration to create a high shear homogenizer, following pumping of the solution through first pump chamber 1610.

Figure 17:
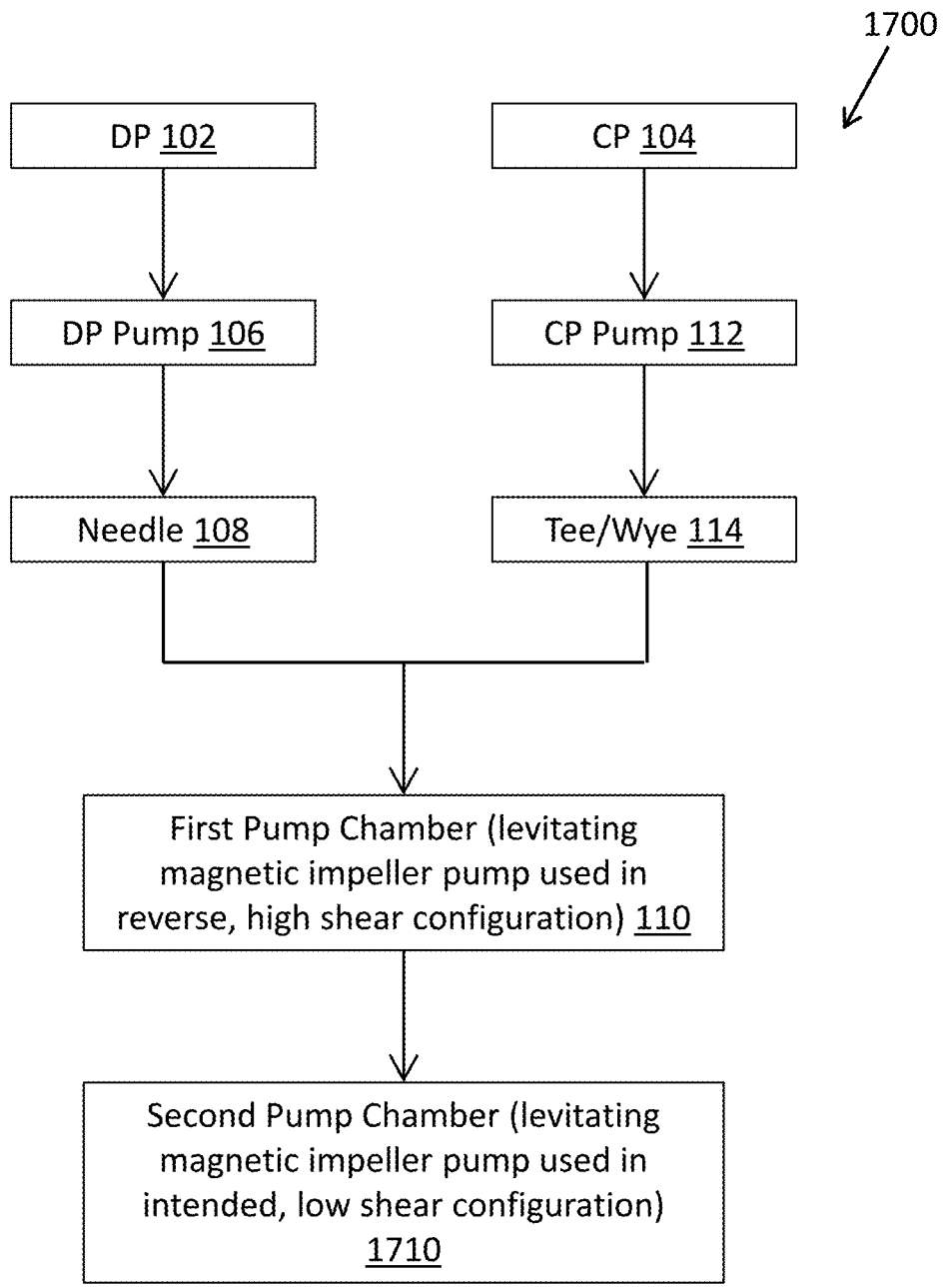
FIG. 17 is a schematic illustrating a system 1700 for producing microspheres.

FIG. 17 is a schematic illustrating a system 1700 for producing microspheres. System 1700 may include a DP source 102 (e.g., a reservoir) operatively connected to a DP pump 106 configured to positively pressurize DP to force DP through a DP needle 108 and into a first pump chamber 110 of a levitating magnetic impeller pump operated in reverse of its intended configuration to create a high shear homogenizer. System 1700 may include a CP source (e.g., a reservoir) operatively connected to a CP pump 112 configured to positively pressurize CP to force CP through a tee/wye 114 and into first pump chamber 110. The contents of first pump chamber 110 is pumped into a second pump chamber 1710 operated in its intended configuration to create a low shear pump, following pumping of the solution through first pump chamber 110.

Figure 18:
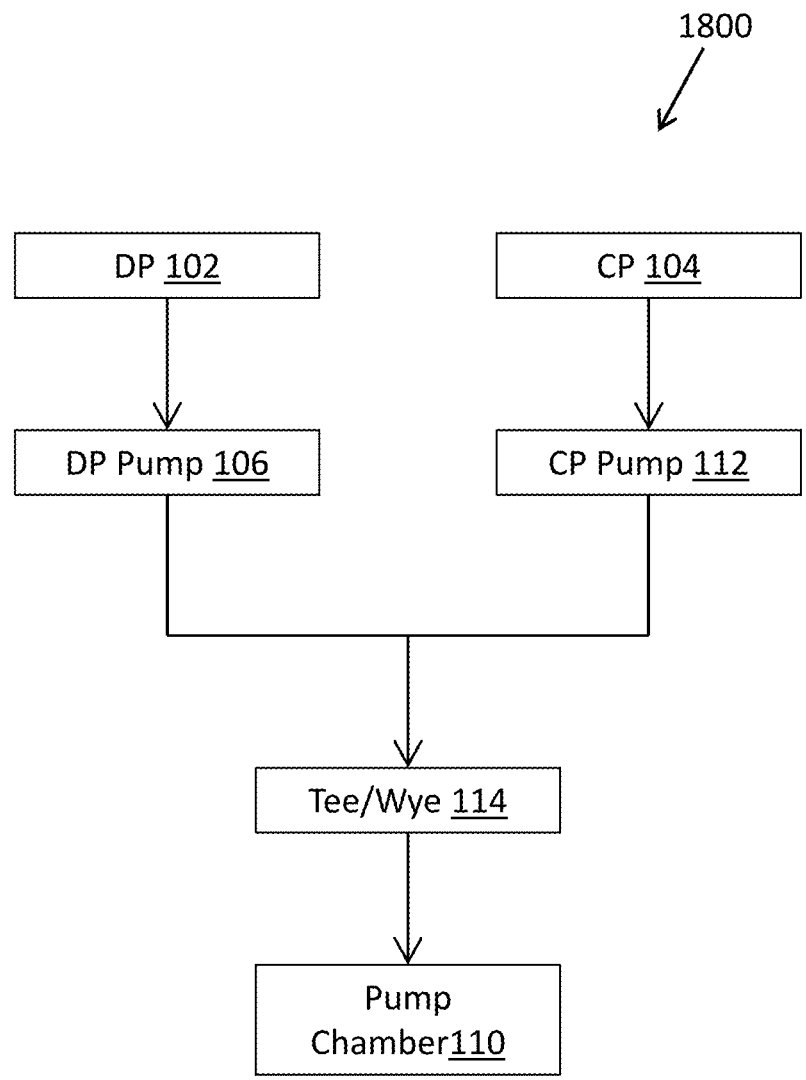
FIG. 18 is a schematic illustrating a system 1800 for producing microspheres.

FIG. 18 is a schematic illustrating a system 1800 for producing microspheres. System 1800 may include a DP source 102 (e.g., a reservoir) operatively connected to a DP pump 106 configured to positively pressurize DP to force DP through a tee/wye 114 and into pump chamber 110. System 1800 may include a CP source (e.g., a reservoir) operatively connected to a CP pump 112 configured to positively pressurize CP to force CP through a tee/wye 114 and into pump chamber 110. The CP and DP first encounter one another within tee/wye 114, and then proceed together into pump chamber 110.

Figure 19:
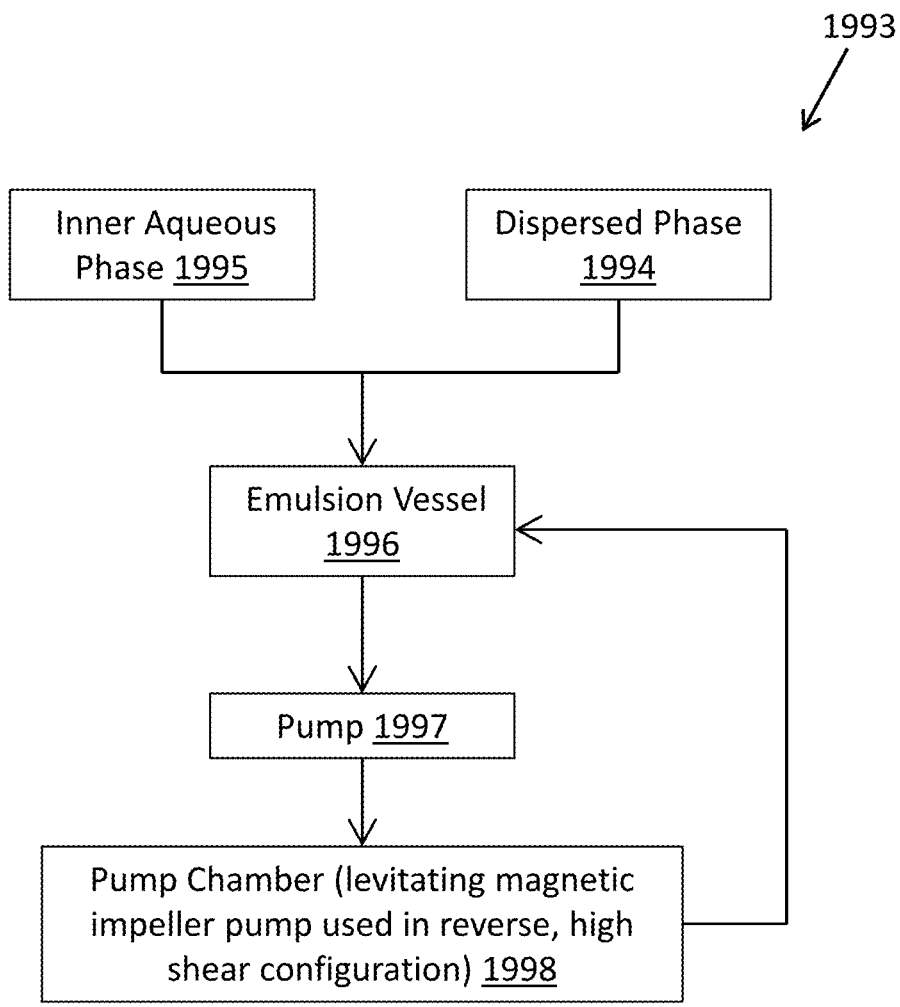
FIG. 19 is a schematic illustrating a system 1993 for manufacturing an emulsion.

FIG. 19 is a schematic illustrating a system 1993 for making an emulsion. Any of the systems and methods described herein may additionally be used to make an emulsion, including for example a primary emulsion or a secondary emulsion, which may include the manufacture of microspheres following preparation of the emulsion. The process to make an emulsion may include using a levitating magnetic impeller pump having a pump chamber 1998, wherein the levitating magnetic impeller pump may be operated in the opposite direction of flow as intended by the manufacture. A DP source 1994 and an inner aqueous phase source 1995 may be provided to supply a DP and an inner aqueous phase to an emulsion vessel 1996. The inner aqueous phase may be or include CP, water, and the like. The mixture may be pumped from emulsion vessel 1996 through a pump 1997 and into the intended output of the levitating magnetic pump into pump chamber 1998, after which the mixture is removed from the intended input of the levitating magnetic pump, and returned to emulsion vessel 1996 to create a circuit. Pump 1997 may be any of a variety of pumps, including for example a peristaltic pump. One or more volume pass throughs may be conducted utilizing the circuit formed as described above, after which a primary emulsion may be observed. That is, the emulsion may pass from emulsion vessel 1996, through pump 1997, through pump chamber 1998 and back to emulsion vessel 1996 one or more times. The inner aqueous phase:DP ratio may be from 1:1-1:80.

In some configurations, the systems described herein always create an emulsion first, followed by the rapid extraction of solvents to make the more solid microspheres. The ratio of the CP and DP entering the pump chamber determines how fast the emulsion droplet solidifies into a microsphere, if it solidifies at all.

Example 1: Placebo Microspheres Produced Using Different Mixing Speeds to Alter Particle Size The process in this example may be used to prepare a microsphere using a polymer with or without an encapsulated drug. These experiments were performed by combining 9.9 g of 75:25 of a poly(lactide-co-glycolide) (PLGA) polymer (7525 4A, commercially available with an inherent viscosity of 0.41 dL/g), 0.1 g of 50:50 PLGA-PEG (5050DLG mPEG5000), and 73.6 g of methylene chloride (DCM) to form the dispersed phase ("DP"), and mixing until the polymers are dissolved.

To create the microspheres, the aqueous continuous phase ("CP") was composed of 0.25% polyvinyl alcohol (PVA) and water. The CP was prepared by heating and mixing the mixture of PVA and water above 70° C. for one hour. After cooling the continuous phase, it was filtered using a 0.2 μm hydrophilic PVDF filter (commercially available).

The DP was pumped simultaneously at a flow rate of 30 mL/min with the CP at a flow rate of 2.0 L/min into the levitating magnetic pump chamber (Levitronix® PurLev-100SU). Two different speeds of the levitating magnetic impeller pump chamber were tested: 2,000 RPM and 3,000 RPM.

After formation, the microspheres entered a solvent removal vessel and were washed with ambient and hot water using a hollow fiber filter (commercially available) to reduce the residual PVA and methylene chloride. This method of solvent extraction is described in U.S. Pat. No. 6,270,802, and is incorporated by reference herein in its entirety.

After washing, the microspheres were dried via lyophilization. The process parameters and particle sizing results are shown in Table 1.

TABLE 1

Process parameter and particle size of placebo batches:

| Batch Number | | 1 | 2 |
|---|---|---|---|
| Mixer Speed (RPM) | | 2,000 | 3,000 |
| Dispersed Phase Flow Rate (mL/min) | | 30 | |
| Continuous Phase Flow Rate (mL/min) | | 2,000 | |
| Particle Size (μm) | 10% CVF | 26 | 17 |
| | 50% CVF | 49 | 34 |
| | 90% CVF | 87 | 75 |

Results proved that microspheres can be created using a magnetic levitating impeller pump as the homogenizer and the size of the microspheres can be manipulated by changing the speed of the impeller. The microspheres were observed via microscopy and no foreign particulate matter was seen.

Example 2: Double Emulsion Batch of Drug-Loaded Microspheres Containing Bovine Serum Albumin (BSA)

The process in this example may use a double emulsion to encapsulate a hydrophilic protein using a magnetic homogenizer. The experiment was performed by combining 4.5 g of 50:50 PLGA (504H, commercially available with an inherent viscosity of 0.57 dL/g) and 75.0 g methylene chloride (DCM) to form a polymer solution. Separately, 0.50 g of bovine serum albumin (BSA) and 6.5 g of deionized water were combined to form the aqueous phase. To create the dispersed phase ("DP"), the polymer solution and the aqueous phase containing the BSA were sonicated together to form an emulsion. The continuous phase ("CP") was composed of 0.35% polyvinyl alcohol (PVA) and water. It was prepared in the same manner as in Example 1.

The DP flow rate into the magnetic homogenization chamber was 37.5 mL/min and the CP flow rate was 3.0 L/min. The mixing speed (impeller speed) of the levitating magnetic impeller pump chamber (Levitronix® PurLev-100SU) was maintained at 2,000 RPM.

After formation, the microsphere suspension was stirred overnight to allow evaporation of the DCM and rinsed while collecting via vacuum filtration to reduce residual solvent levels. The microspheres were dried via lyophilization. The process parameters and results are shown in Table 2.

TABLE 2

Process parameter and results of the BSA-loaded microspheres:

| | | |
|---|---|---|
| Mixer Speed (RPM) | | 2,000 |
| Target Drug load (wt %) | | 10 |
| Dispersed Phase Flow Rate (mL/min) | | 37.5 |
| Continuous Phase Flow Rate (mL/min) | | 3,000 |
| Drug Load (wt/wt %) | | 3.4 |
| Drug encapsulation efficiency (%) | | 34.0 |
| Particle Size (μm) | 10% CVF | 38 |
| | 50% CVF | 91 |
| | 90% CVF | 186 |

Results indicate that microspheres can be created with a double emulsion and with this technology.

Example 3: Solid/Oil/Water (S/O/W) Batch of Drug-Loaded Microspheres Containing Ondansetron This example may use a solid/oil/water (S/O/W) approach to encapsulate a solid, undissolved, API (in this case ondansetron) using the magnetic homogenizer. The experiment was performed by combining 8.0 g of 75:25 PLGA (75 25 DLG 5A-P, commercially available with an inherent viscosity of 0.55 dL/g), 43.3 g DCM, and 2.0 g ondansetron, to create the dispersed phase ("DP"). The ondansetron is partially dissolved and partially suspended in the polymer solution.

The continuous phase ("CP") was composed of 1.0% polyvinyl alcohol (PVA) and water. It was prepared in the same manner as in Example 1.

The DP flow rate into the magnetic homogenization pump chamber was 25 mL/min and the CP flow rate was 1 L/min. The mixing speed (impeller speed) of the levitating magnetic impeller pump chamber was set at 2,250 RPM. After formation, the microspheres were washed in the general method described in Example 1 to reduce the residual DCM. After washing, the microspheres were dried via lyophilization. The process parameters and results are shown in Table 3.

TABLE 3

Process parameters and results of the ondansetron-loaded microspheres:

| | | |
|---|---|---|
| Mixer Speed (RPM) | | 2,250 |
| Target Drug load (wt %) | | 20 |
| Dispersed Phase Flow Rate (mL/min) | | 25 |
| Continuous Phase Flow Rate (mL/min) | | 1,000 |
| Drug Load (wt/wt %) | | 19.9 |
| Drug encapsulation efficiency (%) | | 100 |
| Particle Size (μm) | 10% CVF | 24 |
| | 50% CVF | 48 |
| | 90% CVF | 85 |

Results proved that microspheres can be created with a Solid/Oil/Water method with this technology.

Example 4: Large-Scale Placebo Batch Feasibility

The process may be used for producing a large scale batch of microspheres using the magnetic homogenization chamber where production would be 7.8 kg/hr. The process was performed by combining 650 g of 75:25 PLGA (753H, commercially available with an inherent viscosity of 0.39 dL/g) and 2600 g methylene chloride (DCM) to form the placebo dispersed phase ("DP"). The continuous phase ("CP") was composed of 0.35% polyvinyl alcohol (PVA) and water. It was prepared in the same manner as in Example 1.

The DP flow rate into the magnetic homogenization chamber was 500 mL/min and the CP flow rate was 40.0 L/min. The mixing speed (impeller speed) of the levitating magnetic impeller pump chamber was maintained at 2,000 RPM.

After formation, the microsphere suspension was washed with ambient and hot water through a hollow fiber filter. The process parameters and results are shown in Table 4.

TABLE 4

Process parameters and results for batches manufactured at high flow rates:

| | | |
|---|---|---|
| Mixer Speed (RPM) | | 2,000 |
| Dispersed Phase Flow Rate (mL/min) | | 500 |
| Continuous Phase Flow Rate (mL/min) | | 40,000 |
| Particle Size (μm) | 10% CVF | 15 |
| | 50% CVF | 38 |
| | 90% CVF | 79 |

Results show that microspheres can be created at the high flow rates of 500 mL/min DP and 40 L/min CP with this technology. This batch production equates to 7.8 kg/hr of microspheres being created.

Example 5

In another example, the process was applied with the following results shown in Table 5 using a Levitronix® i100 levitating magnetic impeller pump. The process was performed using PLGA (202H, commercially available) and DCM to form the DP, with a polymer concentration of 10%. The CP was composed of 0.35% PVA and water.

The DP flow rate into the magnetic homogenization chamber was 25 mL/min and the CP flow rate was 2 L/min. The mixing speed (impeller speed) of the levitating magnetic impeller pump chamber was maintained at 1,000 RPM.

TABLE 5

| | | |
|---|---|---|
| Mixer Speed (RPM) | | 1,000 |
| Dispersed Phase Flow Rate (mL/min) | | 25 |
| Continuous Phase Flow Rate (mL/min) | | 2,000 |
| Particle Size (μm) | 10% CVF | 15 |
| | 50% CVF | 34 |
| | 90% CVF | 73 |

The microspheres were observed and no foreign particulate matter was seen.

Example 6

In another example, the process was applied with the following results shown in Table 6 using a Levitronix® i100 levitating magnetic impeller pump. The process was performed using PLGA (202H, commercially available) and DCM to form the DP. The CP was composed of 0.35% PVA and water.

The DP flow rate into the magnetic homogenization chamber was 25 mL/min and the CP flow rate was 2 L/min. The mixing speed (impeller speed) of the levitating magnetic impeller pump chamber was maintained at 4,000 RPM.

TABLE 6

| | | |
|---|---|---|
| Mixer Speed (RPM) | | 4,000 |
| Dispersed Phase Flow Rate (mL/min) | | 25 |
| Continuous Phase Flow Rate (mL/min) | | 2,000 |
| Particle Size (μm) | 10% CVF | 7 |
| | 50% CVF | 15 |
| | 90% CVF | 31 |

The microspheres were observed and no foreign particulate matter was seen.

Example 7

In another example, the process was applied with the following results shown in Table 7 using a Levitronix® i100 levitating magnetic impeller pump. The process was performed using PLGA (202H, commercially available) and DCM to form the DP, with a polymer concentration of 50%. The CP was composed of 0.35% PVA and water.

The DP flow rate into the magnetic homogenization chamber was 25 mL/min and the CP flow rate was 2 L/min. The mixing speed (impeller speed) of the levitating magnetic impeller pump chamber was maintained at 1,000 RPM.

TABLE 7

| | | |
|---|---|---|
| Mixer Speed (RPM) | | 1,000 |
| Dispersed Phase Flow Rate (mL/min) | | 25 |
| Continuous Phase Flow Rate (mL/min) | | 2,000 |
| Particle Size (μm) | 10% CVF | 13 |
| | 50% CVF | 42 |
| | 90% CVF | 83 |

The microspheres were observed and no foreign particulate matter was seen.

Example 8

In another example, the process was applied with the following results shown in Table 8 using a Levitronix® i600 levitating magnetic impeller pump. The process was performed using PLGA (202H, commercially available) and DCM to form the DP. The CP was composed of 0.35% PVA and water.

The DP flow rate into the magnetic homogenization chamber was 100 mL/min and the CP flow rate was 8 L/min. The mixing speed (impeller speed) of the levitating magnetic impeller pump chamber was maintained at 2,000 RPM.

TABLE 8

| Mixer Speed (RPM) | | 2,000 |
|---|---|---|
| Dispersed Phase Flow Rate (mL/min) | | 100 |
| Continuous Phase Flow Rate (mL/min) | | 8,000 |
| Particle Size (μm) | 10% CVF | 9 |
| | 50% CVF | 33 |
| | 90% CVF | 70 |

The microspheres were observed and no foreign particulate matter was seen.

Example 9

In another example, the process was applied with the following results shown in Table 9 using a Levitronix® i100 levitating magnetic impeller pump. The process was performed using PLGA (7525 4A & PEG, commercially available) and DCM to form the DP. The CP was composed of 0.35% PVA and water.

The DP flow rate into the magnetic homogenization chamber was 30 mL/min and the CP flow rate was 2 L/min. The mixing speed (impeller speed) of the levitating magnetic impeller pump chamber was maintained at 2,000 RPM.

TABLE 9

| Mixer Speed (RPM) | | 2,000 |
|---|---|---|
| Dispersed Phase Flow Rate (mL/min) | | 30 |
| Continuous Phase Flow Rate (mL/min) | | 2,000 |
| Particle Size (μm) | 10% CVF | 17 |
| | 50% CVF | 40 |
| | 90% CVF | 74 |

The microspheres were observed and no foreign particulate matter was seen.

Example 10

In another example, the process was applied with the following results shown in Table 10 using a Levitronix® i100 levitating magnetic impeller pump. The process was performed using PLGA (202H, commercially available) and DCM to form the DP. The CP was composed of 0.35% PVA and water.

The DP flow rate into the magnetic homogenization chamber was 400 mL/min and the CP flow rate was 2 L/min. The mixing speed (impeller speed) of the levitating magnetic impeller pump chamber was maintained at 4,000 RPM.

TABLE 10

| Mixer Speed (RPM) | | 4,000 |
|---|---|---|
| Dispersed Phase Flow Rate (mL/min) | | 400 |
| Continuous Phase Flow Rate (mL/min) | | 2,000 |
| Particle Size (μm) | 10% CVF | 7 |
| | 50% CVF | 16 |
| | 90% CVF | 33 |

The microspheres were observed and no foreign particulate matter was seen.

Example 11: Primary Emulsion Followed by Microsphere Manufacture

Figure 20:
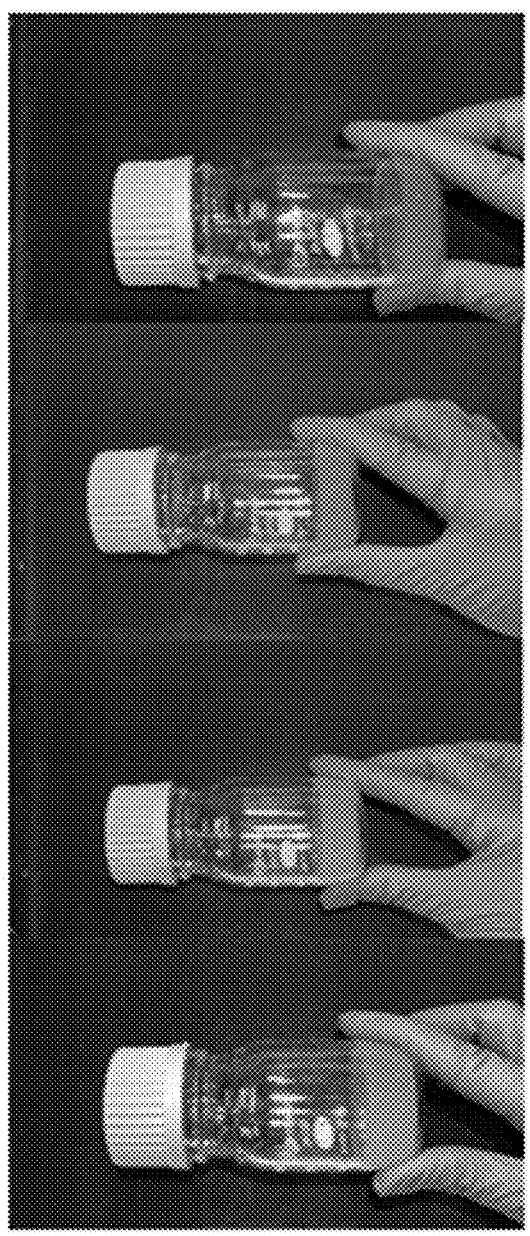
FIG. 20 illustrates (A) a visual progression of a primary emulsion at 0, 1, 2, and 3 hours after 2 volume pass throughs the levitating magnetic impeller pump; and (B) a visual progression of a primary emulsion at 0, 1, 2, and 3 hours after 7 volume pass throughs.
Figure 20:
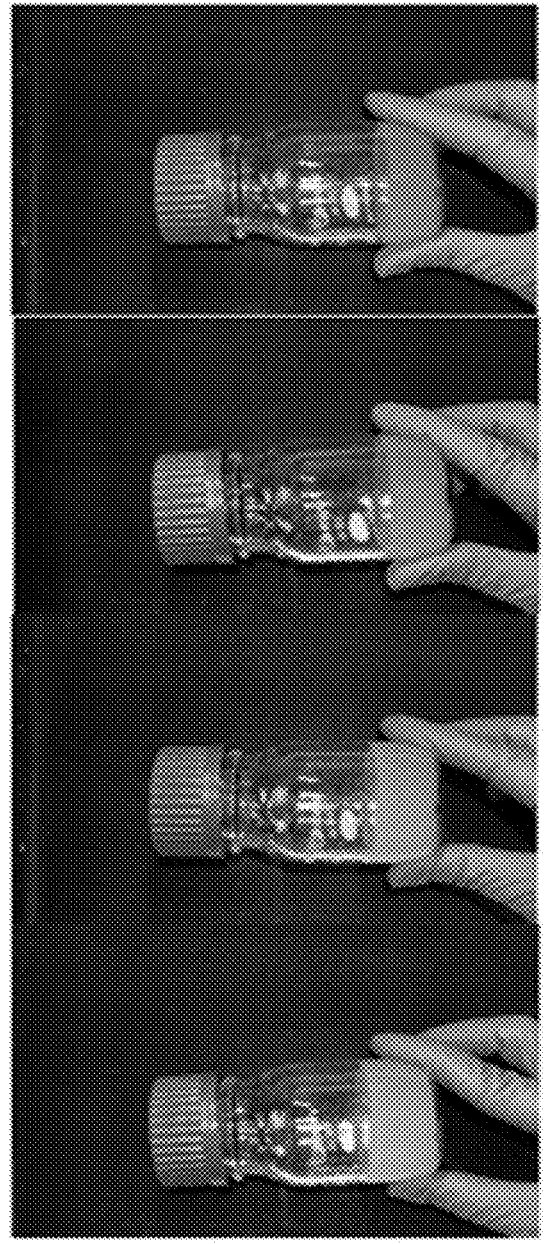

This process includes making a primary emulsion, with the intention to manufacture a microsphere subsequently. This example describes the process to make a primary emulsion using a levitating magnetic impeller pump. The levitating magnetic impeller primary emulsion results were compared to the historic way to make a primary emulsion, i.e. a rotor-stator mixer. For this example, the dispersed phase ("DP") was made in a 1 L bottle containing a cap, 70.0 g 205 S polymer (IV=0.63) was added and dissolved in 387.9 g dichloromethane (DCM) and 46.0 g ethanol (EtOH). Once the polymer was dissolved, the solution was transferred to a top-stirring 1 L vessel, mixing at ~250 RPM. Then, 10.9 mL of the inner aqueous phase, 0.35% poly (vinyl alcohol) in water was added to the vessel. This solution was then pumped through a peristaltic pump at 100 mL/min into the levitating magnetic impeller pump (Levitronix® PuraLev-i100SU) set to 1,000 RPM to begin, and then ramped to 2,000 RPM once solution filled the pump head. The solution was pumped into the levitating magnetic impeller pump in a direction opposite its intended direction of operation, and thus against its natural flow. After 9 minutes, the equivalent of 2 volume passes through the levitating pump, approximately 40 mL were removed from the DP vessel and examined visually and by UV-Vis spectroscopy. A second sample was removed after a total of 31.5 min, the equivalent of 7 volume passes through the levitating magnetic pump, and examined visually and by UV-Vis. Results for visual observation are shown in the images in FIG. 20. FIG. 20 illustrates (A) a visual progression of the primary emulsion at 0, 1, 2, and 3 hours after 2 volume pass throughs the levitating magnetic impeller pump; and (B) a visual progression of the primary emulsion at 0, 1, 2, and 3 hours after 7 volume pass throughs. The primary emulsion was clearly formed with both the 2 and 7 volume pass throughs; this was confirmed by the cloudiness observed in the solution. In addition, 7 volume pass throughs displayed a more stabilized primary emulsion as visually seen at the 3-hour mark after emulsification.

Figure 21:
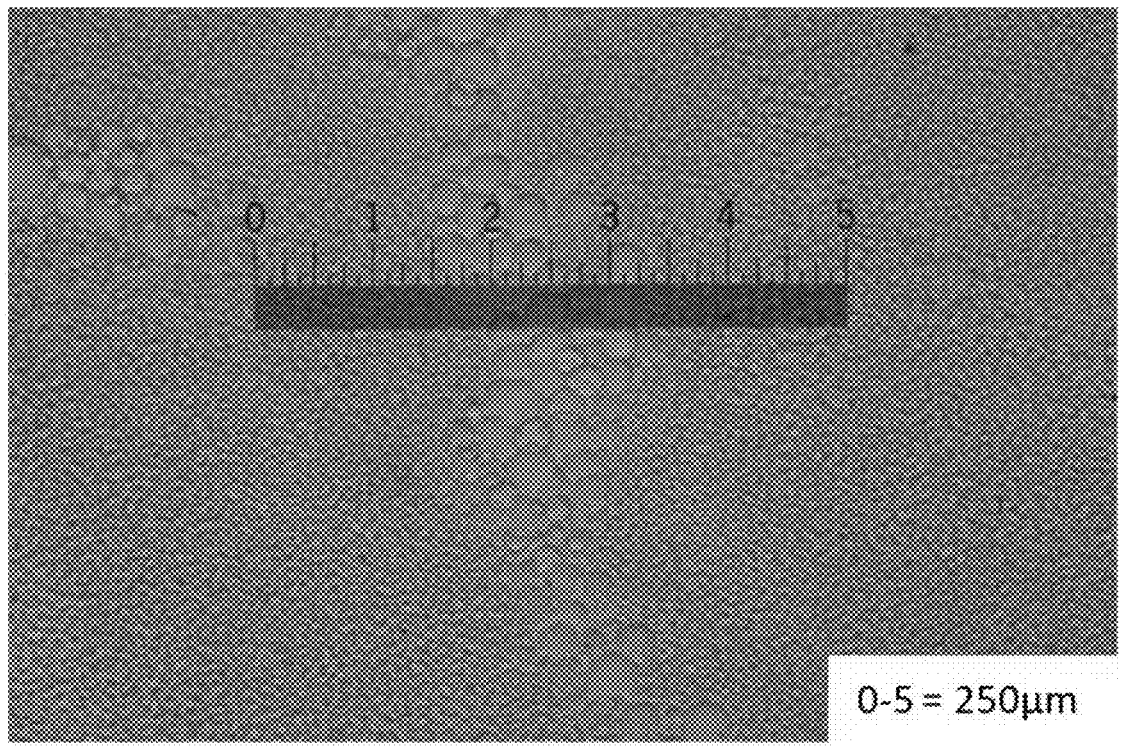
FIG. 21 illustrates a microscopic view of the primary emulsion after 2 volume pass throughs.
Figure 22:
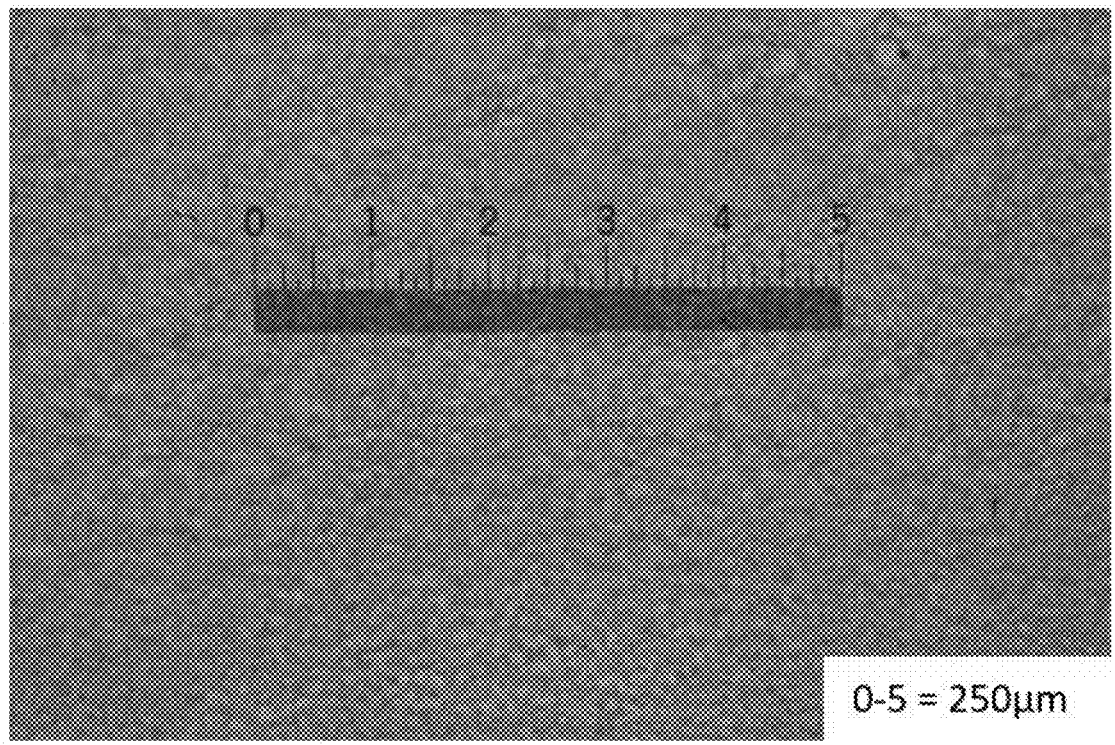
FIG. 22 illustrates a microscopic view of the primary emulsion after 7 volume pass throughs.

FIG. 21 illustrates a microscopic view of the primary emulsion after 2 volume pass throughs. FIG. 22 illustrates a microscopic view of the primary emulsion after 7 volume pass throughs.

Figure 23:
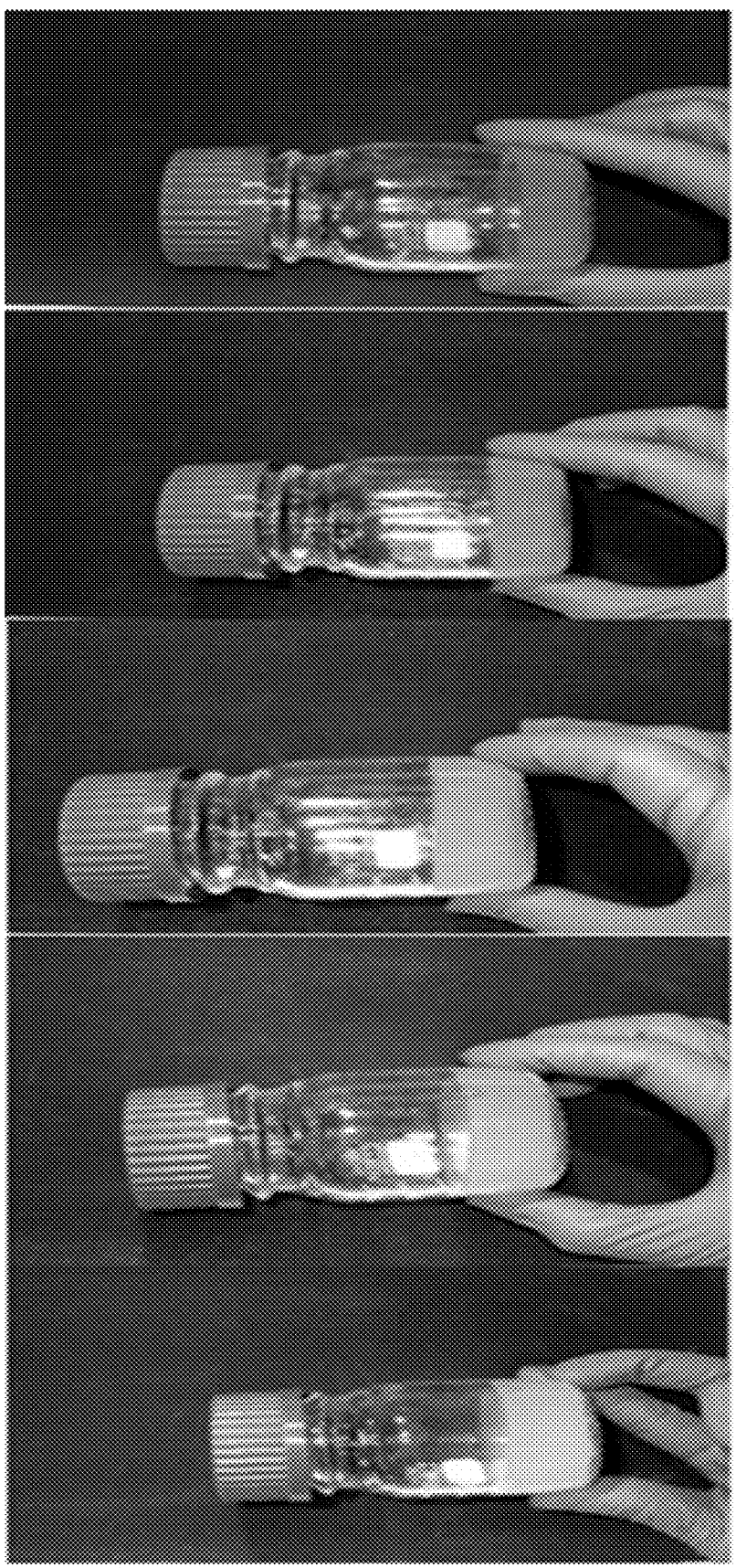
FIG. 23 illustrates a visual progression of a primary emulsion after formation with the Ultra-Turrax® at 0, 1, 2, 3, and 4 hours.

For comparison, an identical, but scaled down DP was made at one-tenth the scale used above. Upon addition of the inner aqueous phase, the primary emulsion was instead made using a rotor-stator homogenizer (Ultra-Turrax® T-25) set to 20,500 RPM and used for 15 seconds, then turned off for 15 seconds, and then homogenized for an additional 15 seconds. Once again, the primary emulsion was observed visually in addition to UV-Vis. FIG. 23 illustrates a visual progression of the primary emulsion after formation with the Ultra-Turrax® at 0, 1, 2, 3, and 4 hours.

As discussed above, UV-Vis was used as a supplement to the visual observations, illustrated in FIG. 24 of the drawings and Table 11 below. Viewing the peak absorption value at the maximum absorption wavelength for each time point, a decrease in absorption value over time was observed. This observation may lead to two conclusions: (1) the primary emulsion was made successfully using a levitating magnetic impeller pump, and (2) the primary emulsion made by the Ultra-Turrax® is similar to that of the levitating magnetic impeller pump. An additional benefit noted, is that the primary emulsion can be tracked by UV-Vis over time to determine how stable that emulsion is depending on length of the emulsifying time.

TABLE 11

Raw values for max absorption wavelength and the corresponding absorption value for all 3 emulsifying methods starting immediately after emulsifying up until 3 or 4 hours post-emulsification. (Max Abs. = maximum absorption wavelength; Abs. Value = absorption value observed).

| Time (hours) | Levitronix® Pump (2 Volume Pass Throughs) | | Levitronix® Pump (7 Volume Pass Throughs) | | Ultra-Turrax® T-25 | |
|---|---|---|---|---|---|---|
| | Max Abs. | Abs. Value | Max Abs. | Abs. Value | Max Abs. | Abs. Value |
| 0 | 258 | 2.405 | 258 | 2.330 | 260 | 2.556 |
| 1 | 256 | 2.128 | 257 | 2.227 | 282 | 2.274 |
| 2 | 256 | 1.915 | 256 | 2.049 | 276 | 2.307 |
| 3 | 256 | 1.985 | 256 | 2.086 | 276 | 2.243 |
| 4 | — | — | — | — | 276 | 2.147 |

Figure 24:
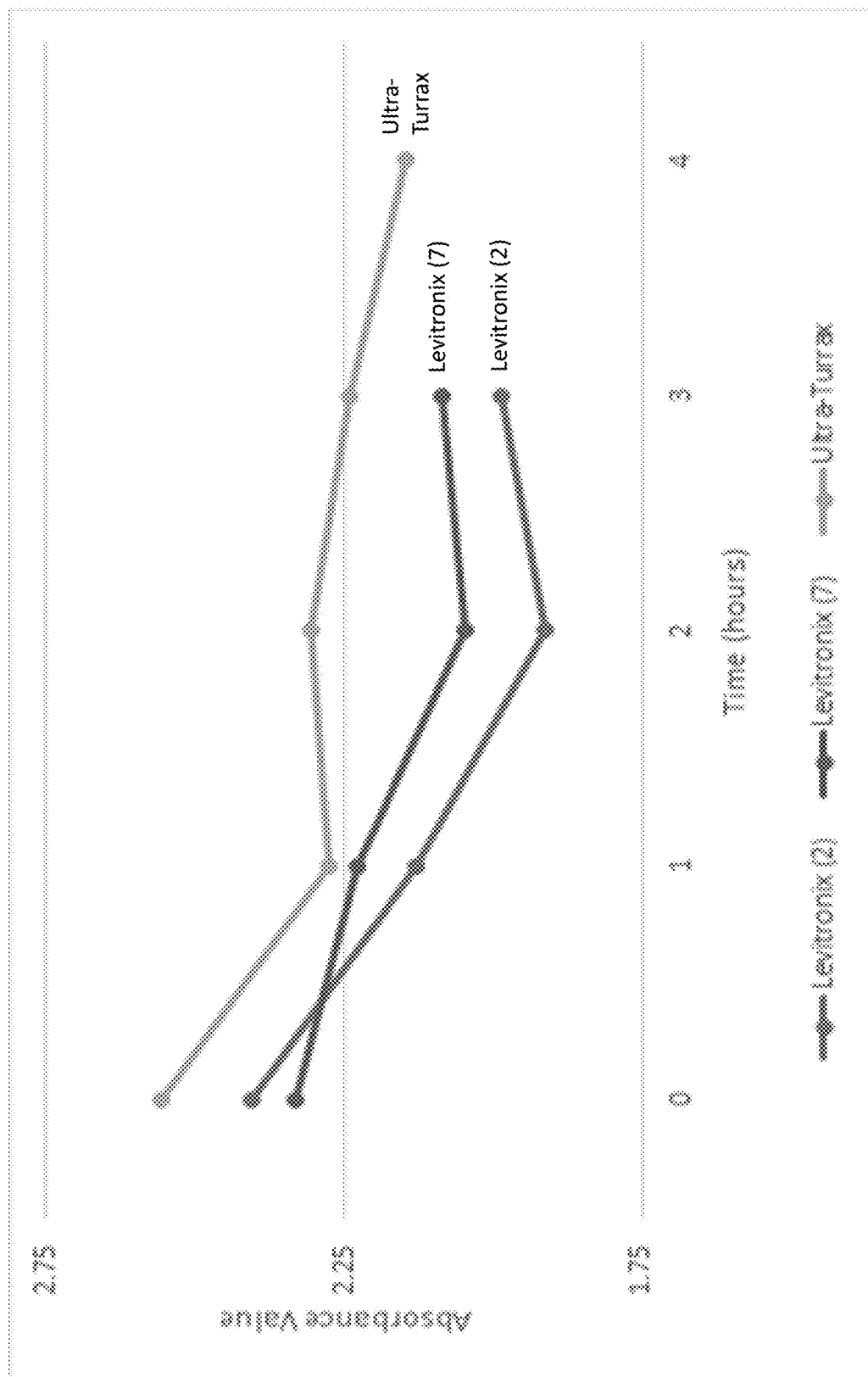
FIG. 24 illustrates a graph representation of absorption values vs. time for all three emulsifying methods described in Example 12.

FIG. 24 illustrates a graph representation of absorption values vs. time for all three emulsifying methods described in Example 11.

Example 12: Use of Levitating Magnetic Impeller Pump in Reverse as High Shear Homogenizer Versus Use of Traditional Homogenizer The use of the levitating magnetic impeller pump in reverse as a high shear homogenizer provides improved results with respect to the elimination and/or mitigation of the presence of foreign particulate matter within a solution following homogenization. Applicant produced microspheres in various test batches using the levitating magnetic impeller pump in reverse as a high shear homogenizer, and upon inspection of the homogenized solutions, identified no or very few foreign particles within the solution.

Use of a standard homogenizer, on the other hand, regularly results in a large volume of small particulate matter. Applicant performed the following test using a traditional high shear in-line homogenizer (rather than the levitating magnetic impeller pump operated in reverse as a high shear homogenizer). In testing a placebo batch created using the traditional homogenizer unit, the total defect percentage for defects classified as major was found to be 6.6%, which greatly exceeds the criteria of not more than 1.5%. Additionally, the total defect percentage was found to be 6.9%, which exceeds the criteria of not more than 5.0%. The majority of the defects categorized as major were small foreign particulate matter. Analysis to identify defects was performed using pre-electron-beam-analysis, post-electron-beam-analysis, and Acceptable Quality Limit inspections. Below are details regarding this test.

Prior to testing, all equipment was cleaned pursuant to normal recommended procedures. The solvent solution was formulated to the target concentration: 52.8 mL Methylene Chloride in 4,000 mL of WFI. The traditional homogenizer was operated at 3,300 RPM for 120 minutes to process 4 L of solution. The resulting solution was filtered for analysis through a filter membrane (Millipore® disk filter, 0.45 μm). The filter membrane was inspected at 4× magnification, which identified foreign particulate all over the filter in a quantity of greater than 100 and too many to accurately count.

A sample of the foreign particulate matter was tested using a stereomicroscope under magnification from 10× to 135×, after which the particles were further analyzed using transmission micro-Fourier transform infrared spectroscopy and for elemental analysis scanning electron microscopy equipped with energy dispersive X-ray spectrometry to determine an identification of the particles. The particles were identified as follows:

TABLE 12

Particle identification.

| Vial | Dark Particles Found | Size (μm) | Identification |
|---|---|---|---|
| 1 | Two similar, brownish-grey particles | 90 | Protein with additional bands suggesting a second unidentified component with steel/steel corrosion (likely 300 series stainless steel) |
| 2 | One orange-brown particle | 90 | Organic char with possible aliphatic hydrocarbon bands (unidentified type) with iron and chromium (likely 300 series stainless steel) |
| 3 | One orange-brown particle | 60 | Organic char with possible aliphatic hydrocarbon bands (unidentified type) with iron and chromium (likely 300 series stainless steel) |
| 4 | One shiny particle | 300 | Teflon® with various iron corrosion products (possibly one or more 300 series stainless steel) |
| 5 | One orange-brown particle, broken when isolated into two parts | 40, 50 | Organic char with possible aliphatic hydrocarbon bands (unidentified type) with iron and chromium (likely 300 series stainless steel) |

The particle identification results were considered to determine a potential source for the particles. Upon further investigation it was determined that the traditional homogenizer's Teflon® shaft bushing and operation of the traditional in-line homogenizer is a cause for the particulate observed in finished products produced using the traditional homogenizer.

Example 13: Use of Levitating Magnetic Impeller Pump in Reverse as High Shear Homogenizer with a Tee/Wye, but without a DP Needle In this example, the elimination of the DP needle was tested, wherein a DP source is pumped directly into a first of three openings in a tee or wye, while a CP source is pumped directly into a second of three openings in a tee or wye, and wherein the solution of the DP and CP leaves the tee or wye via a third of three openings in the tee or wye, which is in fluid communication with an input tube of a pump chamber. This "needleless" system was tested against the same system, including the DP needle as discussed above. The solution is homogenized within the pump chamber, which is a part of a levitating magnetic impeller pump used in a reverse, high shear configuration.

Two dispersed phase (DP) solutions were prepared as follows:

DP 1 was made in a 100 mL bottle using 10.0 g of polymer and 40.0 g of DCM, for a 20% polymer concentration.

DP 2 was made in a 100 mL bottle using 15.0 g of polymer and 60.0 g of DCM, for a 20% polymer concentration.

Three set-ups were tested, as follows:

Test set-up 1 included no DP needle. A tee was connected to the inlet of the levitating magnetic pump. The CP was pumped into the tee via the linear opening of the tee. The DP (DP 1 was used) was pumped into the tee via the perpendicular opening of the tee. The CP was pumped at a rate of 2 L/min. through the tee and into the homogenizer. The DP was pumped at 25 mL/min. through the tee and into the homogenizer. The CP:DP ratio was 80:1. The microspheres were directed from the homogenizer into a 1 L beaker, and approximately 400 mL was collected after 30 seconds of running. The 1 L beaker was stirred until particle size analysis was performed.

Test set-up 2 included no DP needle. The CP was pumped into the tee via the perpendicular opening of the tee. The DP (DP 2 was used) was pumped into the tee via the linear opening of the tee. The flow rates and ratios used were the same as those presented in test set-up 1.

Control set-up 3 included the DP needle. The DP needle was attached to the linear opening of the tee (as described above in reference to FIG. 3, for example) and the DP was pumped through the needle directly into the pump chamber of the homogenizer. The CP was pumped into the tee via the perpendicular opening of the tee (also as described in reference to FIG. 3), and into the homogenizer pump chamber. The flow rates and ratios used were the same as those presented in test set-ups 1 and 2.

Particle size distribution analysis was performed on each of the three set-ups as follows:

Test set-up 1 yielded a d10 value of 37 µm, a d50 value of 73 µm, and a d90 value of 130 µm. Test set-up 2 yielded a d10 value of 37 µm, a d50 value of 69 µm, and a d90 value of 113 µm. Control set-up 3 yielded a d10 value of 35 µm, a d50 value of 66 µm, and a d90 value of 109 µm. As such, the particle size distribution was not affected by the presence or absence of the DP needle in the aforementioned set-ups. All three set-ups produced microspheres.

This indicates the end of the examples included in this application, and the following information does not necessarily pertain to any example.

Figure 25:
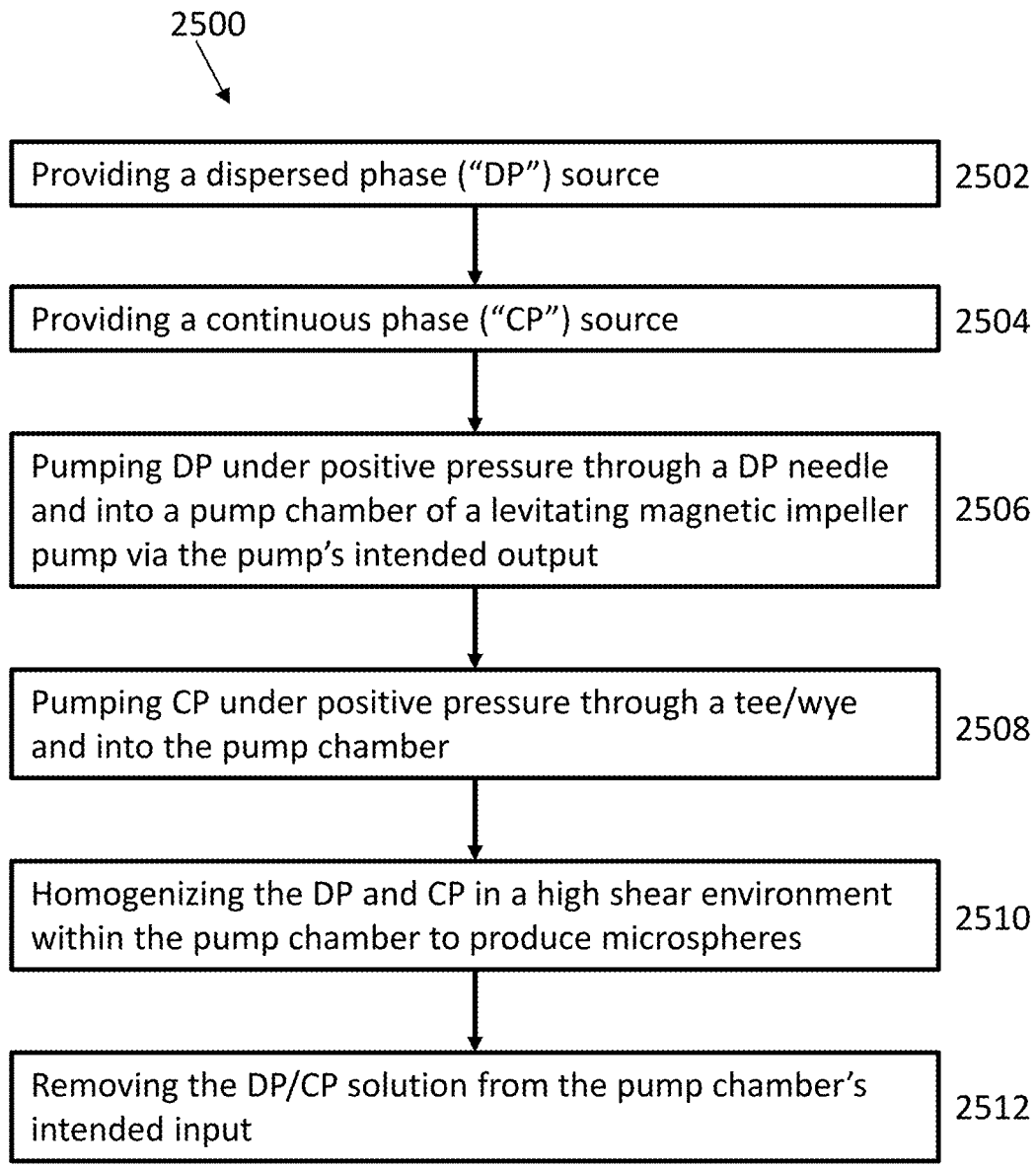
FIG. 25 is a flowchart illustrating an example method for making microspheres utilizing the described system.

FIG. 25 is a flowchart illustrating an example method 2500 for making microspheres utilizing the described system. Method 2500 includes providing a dispersed phase ("DP") source (step 2502); providing a continuous phase ("CP") source (step 2504); pumping DP under positive pressure through a DP needle and into a pump chamber of a levitating magnetic impeller pump via the pump's intended output (step 2506); pumping CP under positive pressure through a tee/wye and into the pump chamber (step 2508); homogenizing the DP and CP in a high shear environment within the pump chamber to produce microspheres (step 2510); and removing the DP/CP solution from the pump chamber's intended input (step 2512). It is understand that in order to utilize the output of the pump chamber as the input, and likewise to use the input of the pump chamber as the output, while running the pump chamber and its corresponding impeller in its normal intended operating direction, the input pressure and/or volume flow rate of the DP and/or CP must be greater than that which would normally be provided at the output of the pump chamber under normal operation. Stated differently, the pressure and/or flow rate of the DP and/or CP must be enough to overcome that provided by the levitating magnetic impeller pump in its normal operation.

The term "fitting" as used herein is intended to represent any of a variety of fittings commonly used in industry in the relevant applications, including a flange, a sanitary fitting, a hose barb, a compression fitting, and the like.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See Bryan A. Garner, A Dictionary of Modern Legal Usage 624 (2d. Ed. 1995). Also, to the extent that the terms "in" or "into" are used in the specification or the claims, it is intended to additionally mean "on" or "onto." To the extent that the term "substantially" is used in the specification or the claims, it is intended to take into consideration the degree of precision available or prudent in manufacturing. To the extent that the term "selectively" is used in the specification or the claims, it is intended to refer to a condition of a component wherein a user of the apparatus may activate or deactivate the feature or function of the component as is necessary or desired in use of the apparatus. To the extent that the term "operatively connected" is used in the specification or the claims, it is intended to mean that the identified components are connected in a way to perform a designated function. As used in the specification and the claims, the singular forms "a," "an," and "the" include the plural. Finally, where the term "about" is used in conjunction with a number, it is intended to include ±10% of the number. In other words, "about 10" may mean from 9 to 11.

As stated above, while the present application has been illustrated by the description of aspects thereof, and while the aspects have been described in considerable detail, it is not the intention of the applicants to restrict or in any way limit the scope of the appended claims to such detail. Additional advantages and modifications will readily appear to those skilled in the art, having the benefit of the present application. Therefore, the application, in its broader aspects, is not limited to the specific details, illustrative examples shown, or any apparatus referred to. Departures may be made from such details, examples, and apparatuses without departing from the spirit or scope of the general inventive concept.

The invention claimed is:

1. A system for forming microspheres, the system comprising:
   a dispersed phase needle having a proximal first end and a distal second end, the dispersed phase needle including:
      a dispersed phase input fitting at the proximal first end,
      a dispersed phase output fitting situated between the dispersed phase input fitting and the distal second end, and
      a needle tube extending from the dispersed phase output fitting to the distal second end,
      wherein the dispersed phase needle comprises a hollow bore throughout its length;
   a tee or a wye including:
      a plurality of tubes,
      a tee input fitting or a wye input fitting,
      a continuous phase input fitting, and
      a continuous phase output fitting situated between the dispersed phase output fitting and the dispersed phase needle's distal second end,
      wherein the tubes each comprise a hollow bore throughout their respective lengths; and
   a chamber, the chamber including:
      an input tube having an input fitting situated adjacent to the dispersed phase needle's distal second end and comprising a hollow bore throughout its length,
      a housing,
      an output tube having an output fitting and comprising a hollow bore throughout its length,
      a hollow interior, and
      an impeller is oriented within the hollow interior,
         wherein the impeller includes a plurality of impeller blades and a base, wherein the base includes a magnet to magnetically engage a rotating magnetic field outside of the chamber, and wherein the impeller rotates and creates a direction of natural flow of a fluid through the chamber in a direction from the output tube toward the input tube.

2. The system of claim 1, wherein the dispersed phase needle output fitting engages the tee input fitting to create a seal.

3. The system of claim 1, wherein the continuous phase output fitting engages the chamber input fitting to create a seal.

4. The system of claim 1, wherein a dispersed phase liquid is pumped through the hollow bore of the dispersed phase needle and into the hollow interior of the chamber in a direction opposite the direction of natural flow, and wherein a continuous phase liquid is pumped through the tee or the wye and into the hollow interior of the chamber in a direction opposite the direction of natural flow, and wherein the dispersed phase liquid and the continuous phase liquid are homogenized in a high shear environment created by rotation of the impeller within the hollow interior of the chamber.

5. The system of claim 1, wherein the dispersed phase needle is oriented through the tee or the wye.

6. The system of claim 1, wherein the tee or the wye is formed from three tubes, wherein two of the three tubes are coaxial in arrangement.

7. The system of claim 1, wherein each of the tubes' hollow bore is in fluid communication with each of the other tubes' hollow bore, the dispersed phase needle's hollow bore, the chamber's input tube's hollow bore, and the chamber's output tube's hollow bore.

8. The system of claim 1, further comprising a pump in fluid communication with the dispersed phase needle's input fitting, the pump configured to exert a pressure that is greater than the pressure of the natural flow.

9. The system of claim 1, further comprising a pump in fluid communication with the tee or the wye's continuous phase input fitting, the pump configured to generate a pressure that is greater than the pressure of the natural flow.

10. The system of claim 1, wherein the hollow interior is free of a rotor, a stator, a bushing, and a gasket.

11. The method of claim 1, wherein the needle tube terminates within the input tube.

* * * * *